(12) United States Patent
Dolensky et al.

(10) Patent No.: US 10,882,003 B2
(45) Date of Patent: Jan. 5, 2021

(54) ROTARY VALVE ASSEMBLY FOR SIEVE BEDS FOR PRESSURE SWING ADSORPTION CONTROL

(71) Applicant: KONINKLIJKE PHILIPS N.V., Eindhoven (NL)

(72) Inventors: Joseph Thomas Dolensky, Kennesaw, GA (US); Robert William Murdoch, Acworth, GA (US)

(73) Assignee: Koninklijke Philips N.V., Eindhoven (NL)

( * ) Notice: Subject to any disclaimer, the term of this patent is extended or adjusted under 35 U.S.C. 154(b) by 171 days.

(21) Appl. No.: 16/306,712

(22) PCT Filed: Jun. 28, 2017

(86) PCT No.: PCT/EP2017/066030
§ 371 (c)(1),
(2) Date: Dec. 3, 2018

(87) PCT Pub. No.: WO2018/002159
PCT Pub. Date: Jan. 4, 2018

(65) Prior Publication Data
US 2019/0126188 A1 May 2, 2019

Related U.S. Application Data

(60) Provisional application No. 62/355,986, filed on Jun. 29, 2016.

(51) Int. Cl.
*B01D 53/047* (2006.01)
*B01D 53/04* (2006.01)
(Continued)

(52) U.S. Cl.
CPC ....... *B01D 53/0446* (2013.01); *A61M 16/101* (2014.02); *B01D 53/047* (2013.01);
(Continued)

(58) Field of Classification Search
CPC .............. A61M 16/101; A61M 16/208; A61M 2202/0208; A61M 2202/0007;
(Continued)

(56) References Cited

U.S. PATENT DOCUMENTS

| 2,944,627 A | 7/1960 | Skarstrom |
| 4,877,429 A | 10/1989 | Hunter |

(Continued)

FOREIGN PATENT DOCUMENTS

| CN | 203784422 U | 8/2014 |
| JP | 04739662 B2 | 8/2011 |

OTHER PUBLICATIONS

DeVilbiss, "Oxygen Therapy", Sunrise Medical, Inc, Canada, 2005, www.sunrisemedical.com.
(Continued)

*Primary Examiner* — Frank M Lawrence, Jr.
(74) *Attorney, Agent, or Firm* — Daniel H. Brean

(57) ABSTRACT

A rotary control valve and a sieve bed module assembly for use in pressure swing adsorption processes to make enriched oxygen product gas for therapy in patients is disclosed. The valve includes a stepping motor with a single shaft extending between ends. At ends of the valve, an air side valve function and oxygen side valve function are provided. Each end includes a stationary plate (stator) with ports, and a disc (rotor) that rotates with the shaft, opening and closing ports to achieve the desired valve function. The valve is integrated into the assembly between two sieve beds and a product storage tank is directly coupled to the oxygen side. Placement of the motor, shaft, and movable parts in the valve and mounting of the beds, valve, and tank in the assembly, result in more compact designs. The motor can be programmed to obtain multiple, different PSA processes and flexibility.

19 Claims, 40 Drawing Sheets

(51) Int. Cl.
*B01D 53/053* (2006.01)
*C01B 13/02* (2006.01)
*A61M 16/10* (2006.01)

(52) U.S. Cl.
CPC ........ B01D 53/053 (2013.01); C01B 13/0259 (2013.01); *A61M 2202/0208* (2013.01); *B01D 53/0423* (2013.01); *B01D 2256/12* (2013.01); *B01D 2257/102* (2013.01); *B01D 2259/40005* (2013.01); *B01D 2259/4533* (2013.01)

(58) Field of Classification Search
CPC ........ C01B 13/0259; C01B 2210/0014; B01D 53/0423; B01D 53/0446; B01D 53/053; B01D 53/047; B01D 2256/12; B01D 2257/102; B01D 2259/40005; B01D 2259/402; B01D 2259/4533
USPC ................ 95/96, 130; 96/121, 124
See application file for complete search history.

(56) References Cited

U.S. PATENT DOCUMENTS

| | | | |
|---|---|---|---|
| 4,925,464 A * | 5/1990 | Rabenau | B01D 53/0423 137/625.29 |
| 5,183,483 A | 2/1993 | Servido et al. | |
| 5,474,595 A | 12/1995 | McCombs | |
| 5,578,115 A * | 11/1996 | Cole | B01D 53/0446 96/121 |
| 5,593,480 A * | 1/1997 | P oschl | B01D 53/0446 96/124 |
| 5,730,778 A | 3/1998 | Hill et al. | |
| 5,891,217 A * | 4/1999 | Lemcoff | B01D 53/0446 95/130 |
| 6,311,719 B1 | 11/2001 | Hill et al. | |
| 6,959,728 B2 | 11/2005 | McCombs et al. | |
| 7,445,663 B1 | 11/2008 | Hunter et al. | |
| 7,524,365 B2 * | 4/2009 | Lin | B01D 53/0415 128/205.24 |
| 7,819,948 B2 | 10/2010 | Wagner | |
| 7,947,118 B2 | 5/2011 | Rarig et al. | |
| 8,272,401 B2 | 9/2012 | McLean | |
| 2005/0132881 A1 | 6/2005 | Baksh et al. | |
| 2007/0137487 A1 | 6/2007 | Whitley et al. | |
| 2009/0107332 A1 * | 4/2009 | Wagner | F16K 11/074 95/100 |
| 2011/0247620 A1 | 10/2011 | Armstrong et al. | |
| 2017/0014748 A1 * | 1/2017 | Li | B01D 53/0446 |

OTHER PUBLICATIONS

Philips SimplyGo Portable oxygen concentrator, https://www.usa.philips.com/healthcare/product/HC1068987/simplygo-portable-oxygen-concentrator, Accessed Dec. 3, 2018.

* cited by examiner

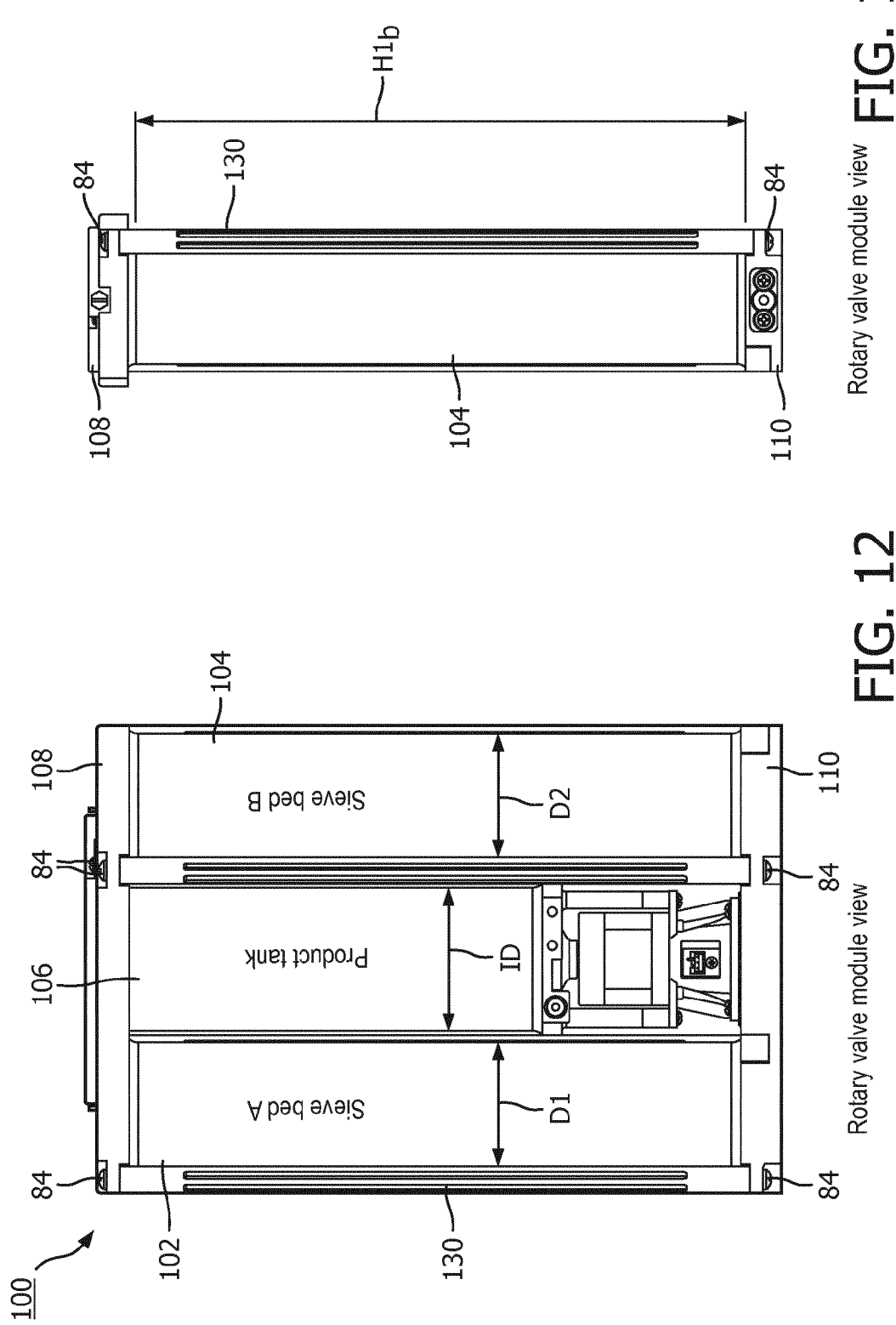

Rotary valve module compact triangle embodiment

Rotary valve module compact triangle embodiment

Config 1: 4-steps ASB process and rotors

| Example | 4 step air side balance process | | | | | | |
|---|---|---|---|---|---|---|---|
| | | Home Step 1 | Step 2 | Step 3 | Step 4 | Total | |
| | Shaft angle | 0 | 90 | 180 | 270 | 360 | degrees |
| | Step time | 5.00 | 0.80 | 5.00 | 0.80 | 11.60 | Cycle time (sec.) |
| | Equiv. valves | | | | | | |
| | Feed A | ▨ | ▨ | | ▨ | | |
| | Feed B | | ▨ | ▨ | | | |
| | Exh A | | | ▨ | | | |
| | Exh B | ▨ | | | | | |

FIG. 25

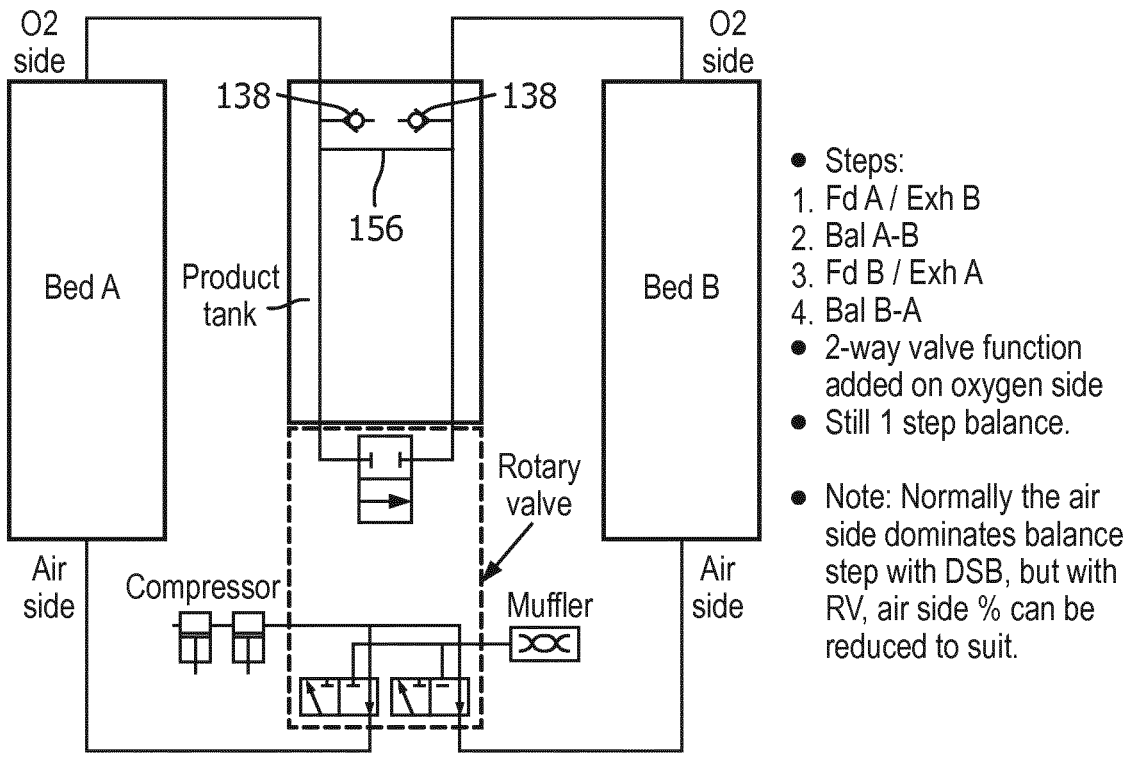

Config 2. 4-step double side balance

- Steps:
  1. Fd A / Exh B
  2. Bal A-B
  3. Fd B / Exh A
  4. Bal B-A
- 2-way valve function added on oxygen side
- Still 1 step balance.

- Note: Normally the air side dominates balance step with DSB, but with RV, air side % can be reduced to suit.

Double side balance process
rotary valve equivalent to two 3-way valves + one 2-way valve
Ref: EcoFlo w/SAAC/ASCO valve + asco sciencivic valve

FIG. 26

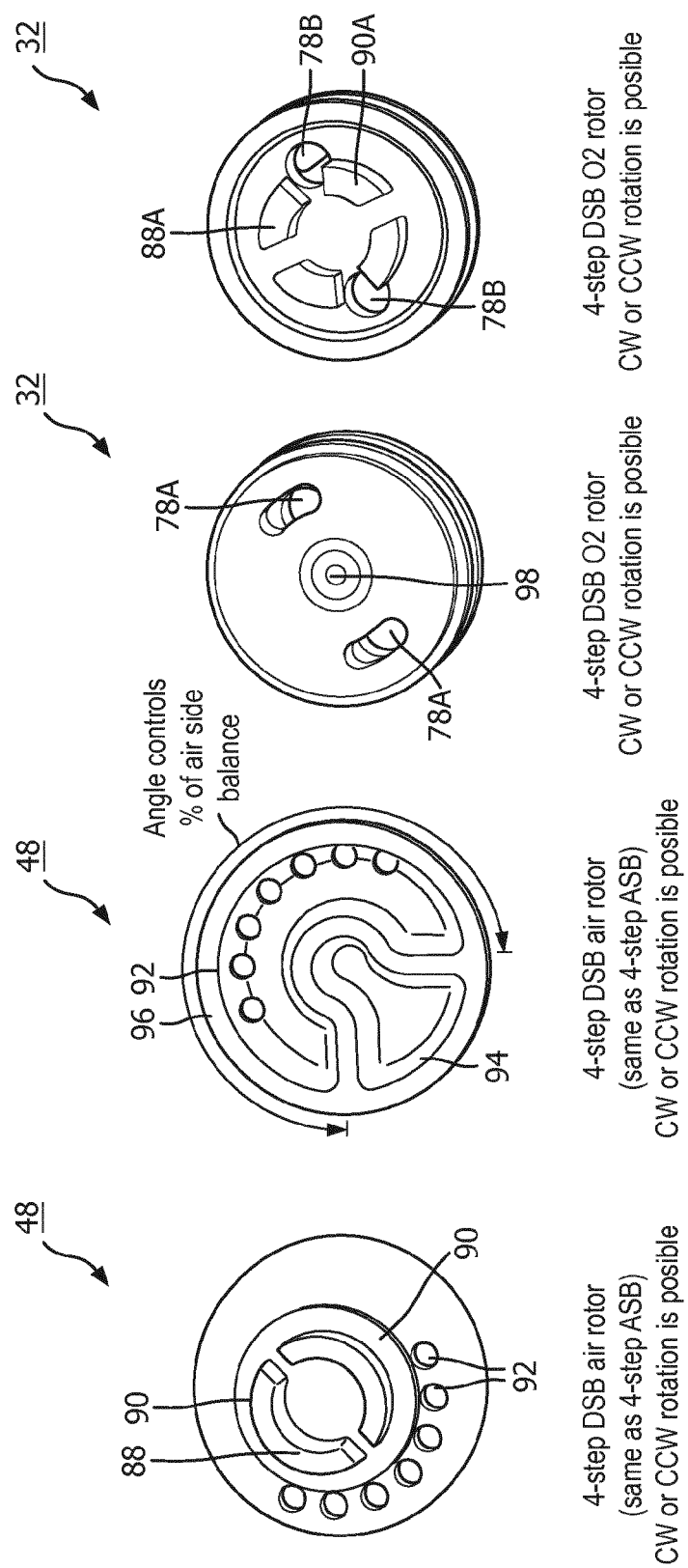

Config 2: 4-step DSB process and rotors

| | | Home | | | | Total | |
|---|---|---|---|---|---|---|---|
| | | Step 1 | Step 2 | Step 3 | Step 4 | | |
| Example | 4 step double side balance process | | | | | | |
| | Shaft angle | 0 | 90 | 180 | 270 | 360 | degrees |
| | Step time | 5.00 | 0.60 | 5.00 | 0.60 | 11.20 | Cycle time (sec.) |
| | Equiv. valves | | | | | | |
| | Feed A | ▓ | | | ▓ | | |
| | Feed B | | ▓ | ▓ | | | |
| | Exh A | | | ▓ | ▓ | | |
| | Exh B | ▓ | | | | | |
| | Balance | | ▓ | | ▓ | | |

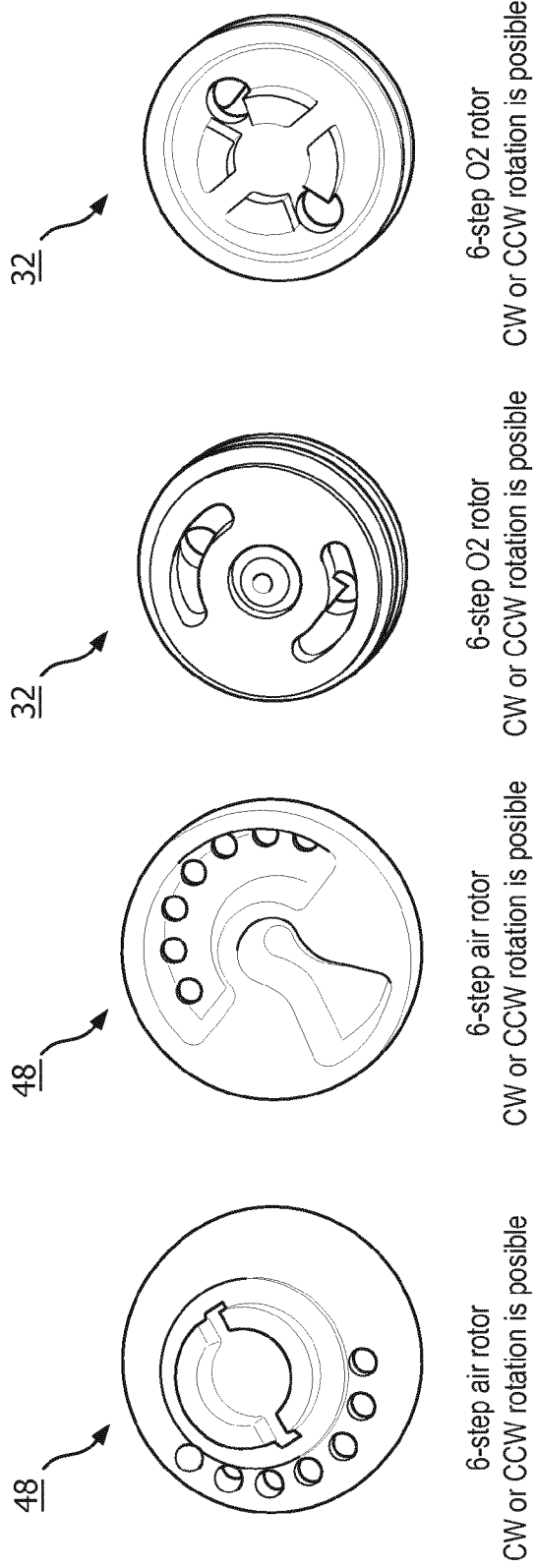

Config 3: 6-step OSB RV process and rotors 6 step O2 side balance process

| | | Home | | | | | | | Total | |
|---|---|---|---|---|---|---|---|---|---|---|
| | | Step 1 | Step 2 | Step 3 | Step 4 | Step 5 | Step 6 | | | |
| | Shaft angle | 0 | 60 | 120 | 180 | 240 | 300 | | 360 | degrees |
| Example | Step time | 5.00 | 0.40 | 0.40 | 5.00 | 0.40 | 0.40 | | 11.60 | Cycle time (sec.) |
| | Equiv. valves | | | | | | | | | |
| | Feed A | ▨ | ▨ | | | | | | | |
| | Feed B | | | | ▨ | ▨ | ▨ | | | |
| | Exh A | | | | ▨ | ▨ | | | | |
| | Exh B | ▨ | | | | | ▨ | | | |
| | Balance | | ▨ | ▨ | | | ▨ | | | |

True OSB process = no overlapping feed valves

FIG. 37

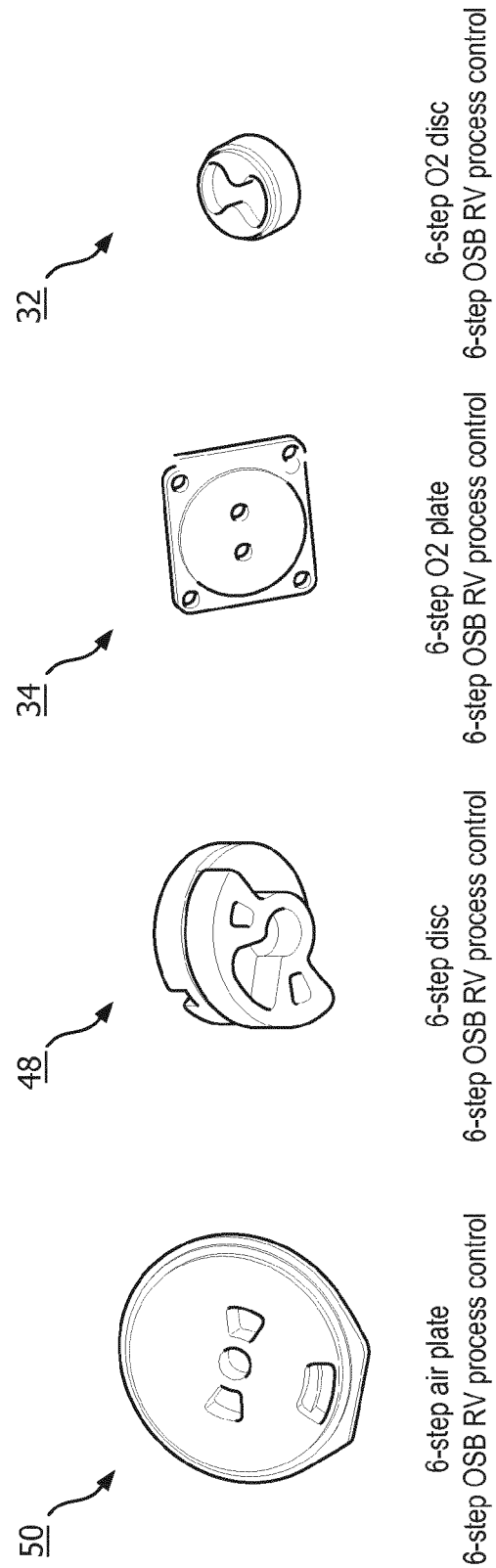

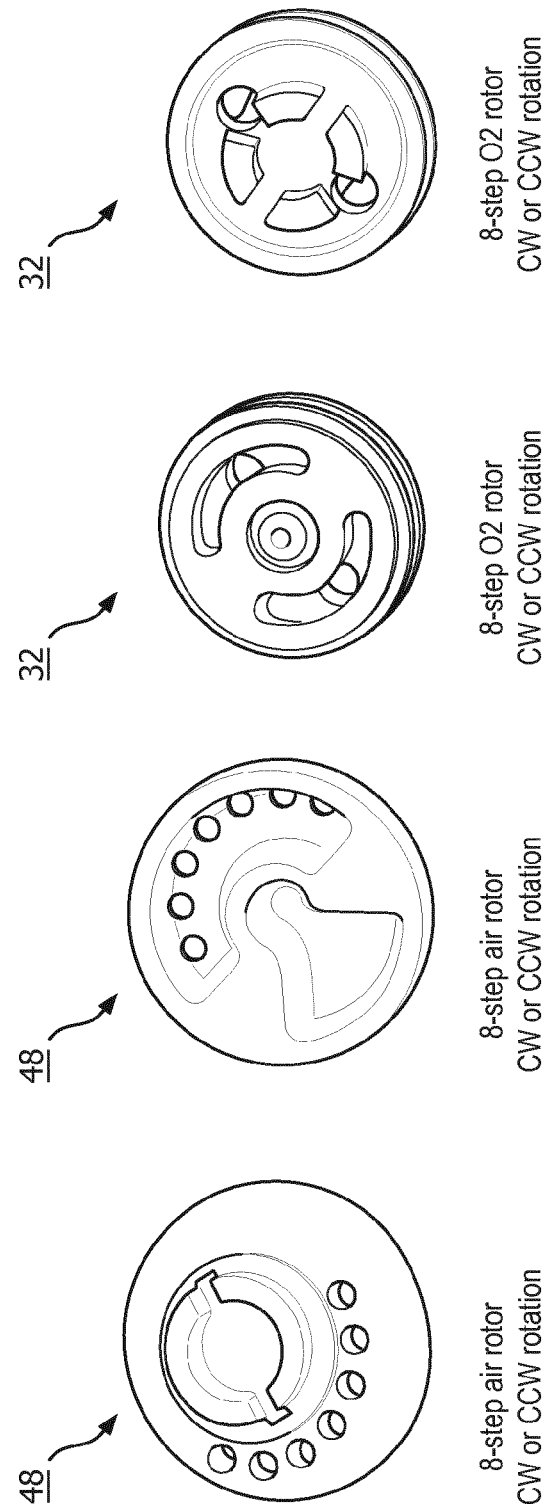

Config 4: 8-step OSB RV process and rotors

| Example | | Home<br>Step 1 | Step 2 | Step 3 | Step 4 | Step 5 | Step 6 | Step 7 | Step 8 | Total |
|---|---|---|---|---|---|---|---|---|---|---|
| | Shaft angle | 0 | 45 | 90 | 135 | 180 | 225 | 270 | 315 | 360 degrees |
| | Step time | 3.00 | 1.75 | 0.50 | 0.80 | 3.00 | 1.75 | 0.50 | 0.80 | 12.10 Cycle time (sec.) |
| | Equiv. valves | | | | | | | | | |
| | Feed A | ▓ | ▓ | ▓ | | | | | | |
| | Feed B | | | | | ▓ | ▓ | ▓ | | |
| | Exh A | | | | | ▓ | ▓ | ▓ | | |
| | Exh B | ▓ | ▓ | ▓ | | | | | | |
| | Purge/balance | | | | ▓ | | | | ▓ | |

8 step O2 side balance process

FIG. 51

10-step OSB RV process control 10 step O2 side balance process - step time approx.

| Example | | Home | Step 1 | Step 2 | Step 3 | Step 4 | Step 5 | Step 6 | Step 7 | Step 8 | Step 9 | Step 10 | Total | |
|---|---|---|---|---|---|---|---|---|---|---|---|---|---|---|
| | Shaft angle | | 0 | 36 | 72 | 108 | 144 | 180 | 216 | 252 | 288 | 324 | 360 | degrees |
| | Step time | | 1.00 | 2.00 | 2.00 | 0.40 | 0.40 | 1.00 | 2.00 | 2.00 | 0.40 | 0.40 | 11.60 | Cycle time (sec.) |
| | Equiv. valves | | | | | | | | | | | | | |
| | Feed A | | | | | ▨ | ▨ | ▨ | ▨ | ▨ | ▨ | ▨ | | |
| | Feed B | | ▨ | ▨ | ▨ | ▨ | ▨ | ▨ | | | | | | |
| | Exh A | | | | ▨ | | | | | | | | | |
| | Exh B | | ▨ | ▨ | | | | | | | | | | |
| | Purge A | | | | | | | ▨ | | | | | | |
| | Purge B | | | | | | | | | | | | | |
| | Balance | | | | | ▨ | ▨ | | | ▨ | ▨ | | | |

OSB process = no overlapping feed valves and exh valves closed during balance steps CW rotation shown

FIG. 61

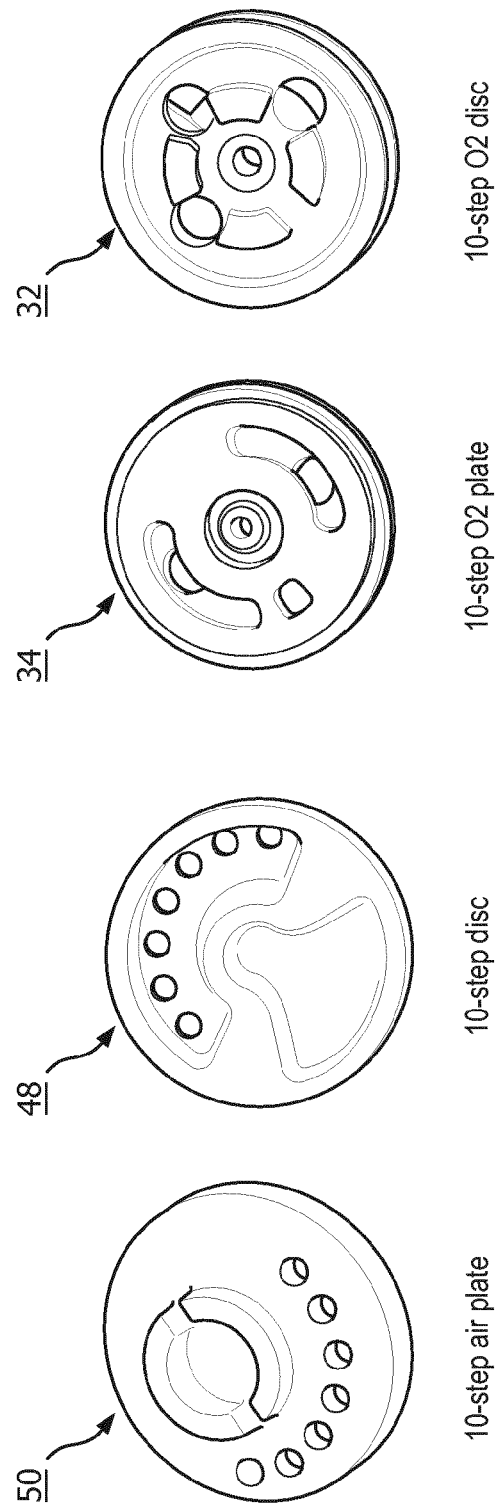

ROTARY VALVE ASSEMBLY FOR SIEVE BEDS FOR PRESSURE SWING ADSORPTION CONTROL

CROSS-REFERENCE TO PRIOR APPLICATIONS

This application claims the priority benefit under 35 U.S.C. § 371 of International Patent Application No. PCT/EP2017/066030, filed on 28 Jun. 2017, which claims the priority benefit of U.S. Provisional Patent Application No. 62/355,986, filed on 29 Jun. 2016, the contents of which are herein incorporated by reference.

BACKGROUND OF THE INVENTION

1. Field of the Invention

The present disclosure is generally related to oxygen concentrators, and in particular oxygen concentrators utilizing a rotary control valve for pressure swing adsorption (PSA) control, and methods relating thereto.

2. Description of Related Art

Oxygen concentrators are devices that use a source of compressed air, a molecular sieve (typically in the form of two sieve columns), and a pressure swing adsorption (PSA) process. Generally, the oxygen concentrators generate approximately 1-10 liters/minute of 86%-96% oxygen gas for oxygen therapy. U.S. Pat. No. 2,944,627 to Skarstrom describes an example of an early gas fractionalization method which can concentrate oxygen from air using molecular sieve and PSA process. U.S. Pat. No. 5,474,595 to McCombs describes an example of a known oxygen concentrator utilizing four solenoid valves on the air side and a single solenoid valve on the product side. U.S. Pat. No. 5,183,483 to Servido, et. al describes an example simplified pneumatic circuit for an oxygen concentrator that uses two 3-way solenoid valves on the air side and air side sieve bed pressure balancing to reduce the complexity and number of valves necessary to control a PSA process.

Many different PSA process cycles have been developed over the years, from two steps to ten or more steps per two-bed cycle, and each process requires a sufficient number of valve functions to control the flow of gas (according to the process definition).

Traditionally, when designing a product for high volume production, any advantages of the more complex PSA processes are typically measured against the cost, size, weight and reliability of the additional valves required. Often this costs-benefit analysis results in valves being eliminated, thus sacrificing PSA process efficiency and flexibility. In the case where PSA process efficiency benefits are required, the costs and complexity of adding multiple valves are accepted as an undesirable trade-off. The present disclosure addresses many of the shortcomings of the prior art.

SUMMARY OF THE INVENTION

It is an aspect of this disclosure to provide a rotary control valve. The rotary control valve has a product end comprising a product rotor and a product stator, and an air end comprising an air rotor and an air stator. The product rotor includes a plurality of cavities configured for alignment with ports in the product stator, and the air rotor includes a plurality of cavities configured for alignment with ports in the air stator. A shaft is operatively connected to the product rotor and the air rotor. A motor is configured to drive the shaft. The driving of the shaft is configured to rotate the product rotor and air rotor relative to their respective stators such that cavities in each of the rotors selectively align with ports in their respective stators.

Another aspect provides a module assembly. The module assembly includes a rotary control valve that has a product end comprising a product rotor and a product stator, and an air end comprising an air rotor and an air stator. The product rotor includes a plurality of cavities configured for alignment with ports in the product stator, and the air rotor includes a plurality of cavities configured for alignment with ports in the air stator. A shaft is operatively connected to the product rotor and the air rotor. A motor is configured to drive the shaft. The driving of the shaft is configured to rotate the product rotor and air rotor relative to their respective stators such that cavities in each of the rotors selectively align with ports in their respective stators. The module assembly also includes a sieve bed module configured to receive air from the rotary control valve and to output product gas.

Yet another aspect provides a method for controlling a pressure swing adsorption (PSA) process using a rotary control valve that has a product end and an air end, the product end having a product rotor and a product stator and an air end having an air rotor and an air stator. The product rotor includes a plurality of cavities configured for alignment with ports in the product stator and the air rotor includes a plurality of cavities configured for alignment with ports in the air stator. The rotary control valve further includes a shaft operatively connected to the product rotor and the air rotor, and a motor configured to drive the shaft. The method includes operating the motor; driving the shaft using the motor; and rotating the product rotor and the air rotor relative to their respective stators as a result of the driving of the shaft. The rotating of the product rotor and air rotor selectively aligns cavities in the rotors with ports of their respective stators.

In accordance with embodiments, the motor can be programmed and controlled to move clockwise, or counter-clockwise, continuously, or intermittently in steps, at low, high, or variable speeds to obtain multiple, different, PSA processes resulting in high degree of PSA process design flexibility.

Other aspects, features, and advantages of the present disclosure will become apparent from the following detailed description, the accompanying drawings, and the appended claims.

BRIEF DESCRIPTION OF THE DRAWINGS

FIGS. 12, 13, 14, and 15 show a front side, end, back side, and bottom view of the module assembly of FIG. 11;

FIG. 25 is a chart illustrating feeds and exhausts of the beds in the assembly at each of the steps of the 4-step process of FIG. 22;

FIG. 26 illustrates a schematic diagram of valves replaced by the disclosed rotary control valve for a 4-step double side PSA process in the disclosed assembly, in accordance with an embodiment;

FIGS. 27 and 28 show a first side and a second side, respectively, of an exemplary rotor for use in the rotary control valve on its second side during the 4-step process of FIG. 26, in accordance with an embodiment;

FIGS. 29 and 30 show a first side and a second side, respectively, of an exemplary rotor for use in the rotary control valve on its first side during the 4-step process of FIG. 26, in accordance with an embodiment;

FIGS. 33 and 34 show a first side and a second side, respectively, of an exemplary rotor for use in the rotary control valve on its second side during the 6-step process of FIG. 32, in accordance with an embodiment;

FIGS. 35 and 36 show a first side and a second side, respectively, of an exemplary rotor for use in the rotary control valve on its first side during the 6-step process of FIG. 32, in accordance with an embodiment;

FIG. 37 is a chart illustrating the feeds, exhausts, and balancing of the beds in the assembly at each of the steps in the 6-step process of FIG. 32;

FIGS. 38 and 39 show a first side and a second side, respectively, of an exemplary rotor for use in the rotary control valve on its second side during the 6-step process of FIG. 32, in accordance with another embodiment;

FIGS. 40 and 41 show a first side and a second side, respectively, of an exemplary rotor for use in the rotary control valve on its first side during the 6-step process of FIG. 32, in accordance with another embodiment;

FIGS. 47 and 48 show a first side and a second side, respectively, of an exemplary rotor for use in the rotary control valve on its second side during the 8-step process of FIG. 46, in accordance with an embodiment;

FIGS. 49 and 50 show a first side and a second side, respectively, of an exemplary rotor for use in the rotary control valve on its first side during the 8-step process of FIG. 46, in accordance with an embodiment;

FIG. 51 is a chart illustrating the feeds, exhausts, and purging and balancing of the beds in the assembly at each of the steps during the 8-step process of FIG. 46;

FIG. 61 is a chart illustrating the feeds, exhausts, purging, and balancing of the beds in the assembly at each of the steps during the 10-step process of FIG. 60;

FIGS. 62 and 63 show a first side and a second side, respectively, of an exemplary rotor for use in the rotary control valve on its second side during the 10-step process of FIG. 60, in accordance with another embodiment; and FIGS. 64 and 65 show a first side and a second side, respectively, of an exemplary rotor for use in the rotary control valve on its first side during the 10-step process of FIG. 60, in accordance with another embodiment.

DETAILED DESCRIPTION OF THE PREFERRED EMBODIMENT(S)

Figure 1:
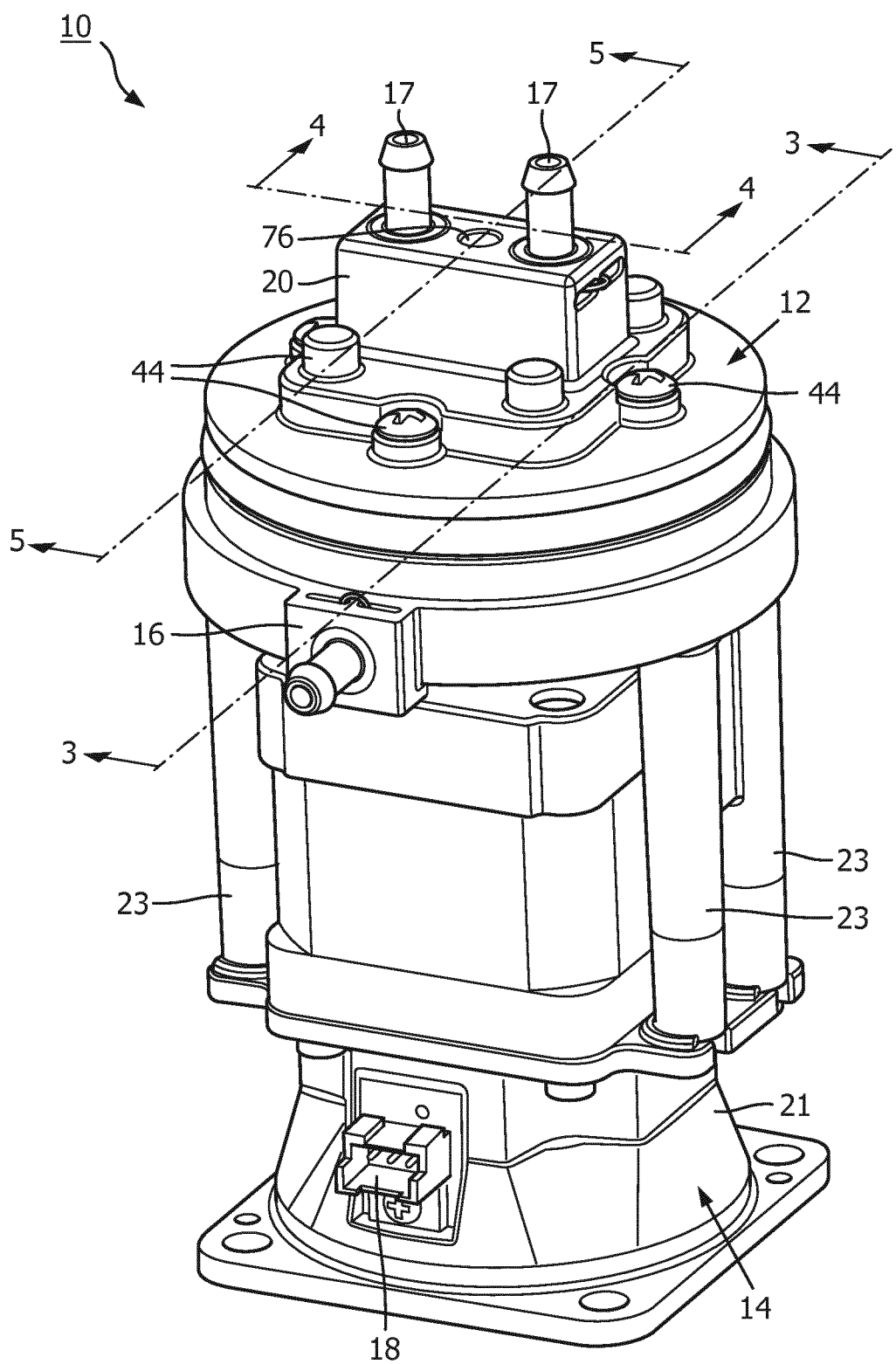
FIG. 1 is a top plan view of a rotary control valve in accordance with an embodiment.
Figure 2:
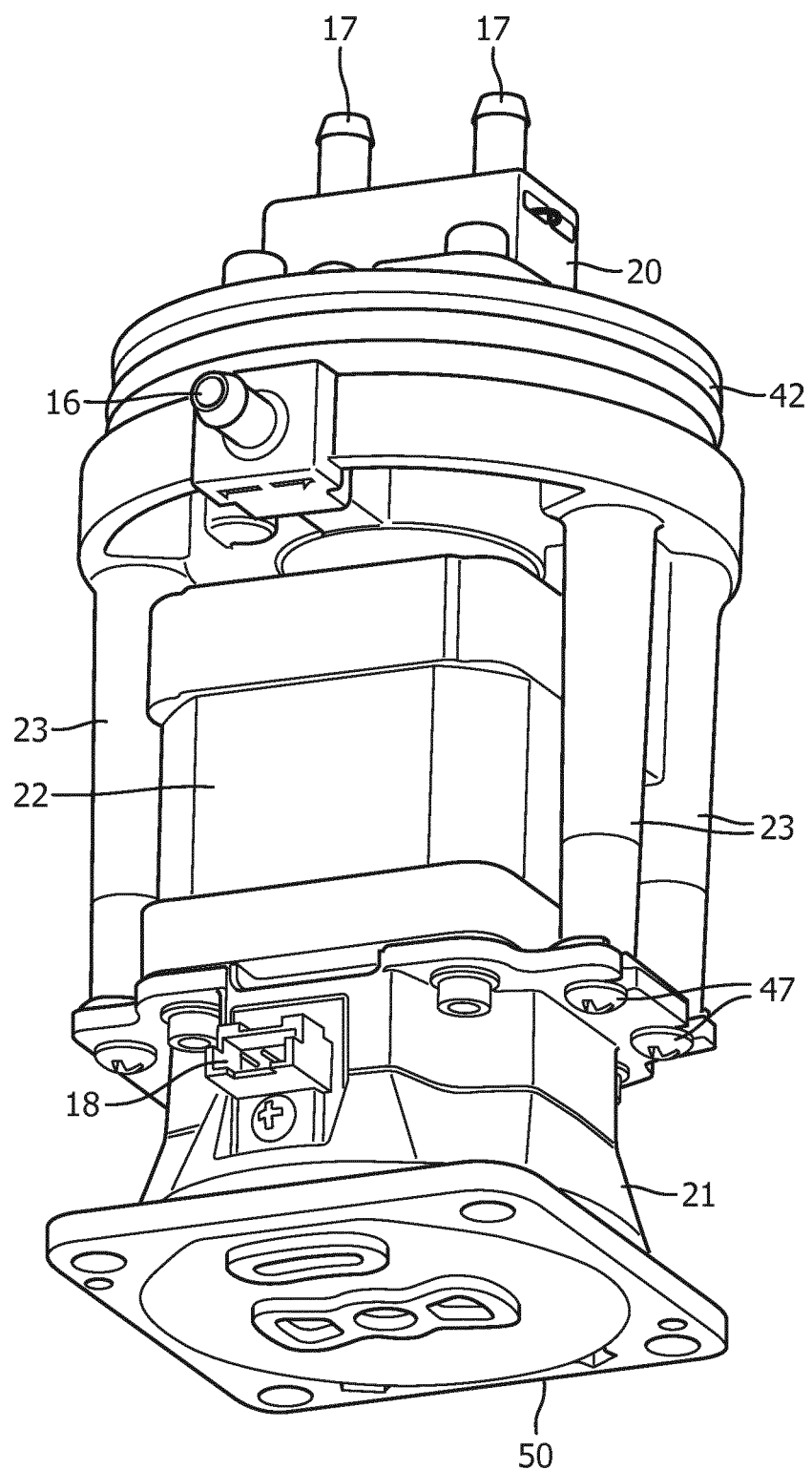
FIG. 2 is a bottom plan view of the rotary control valve of FIG. 1.

The disclosed rotary control valve and a molecular sieve bed module assembly is described herein as being used in pressure swing adsorption (PSA) processes, or a control flow processes or cycles, that are commonly used to make enriched product gas, e.g., oxygen (O2). Such gas can be used, for example, in an O2 concentrator for delivery of oxygen drug therapy to patients. Generally, the molecular sieve bed module assembly generates approximately 86%-96% oxygen gas for oxygen therapy.

However, it should be understood that other types of devices for making enriched product gas may implement a rotary valve or pressure swing adsorption process as disclosed herein, and thus should not be limited to the described implementations.

FIGS. 1-5 illustrate one embodiment of a rotary control valve 10 for controlling a desired PSA process in a module assembly, such as an oxygen concentrator. The rotary control valve has a connector 16 for pressure sensing and an electrical connector 18 for powering and controlling the motor. The rotary control valve 10 has a product end 12 at its top end and an air end 14 at its bottom end, and a motor 22 with a single shaft 24 extending in a vertical direction (vertical axis A) between both ends. The motor 22 drives the shaft 24, for example, about the axis A. As the shaft 24 is rotated, internal components within housings 20, 21 at the ends 12, 14 of the valve 10 are opened and closed to achieve the desired valve function, as explained below.

Figure 3:
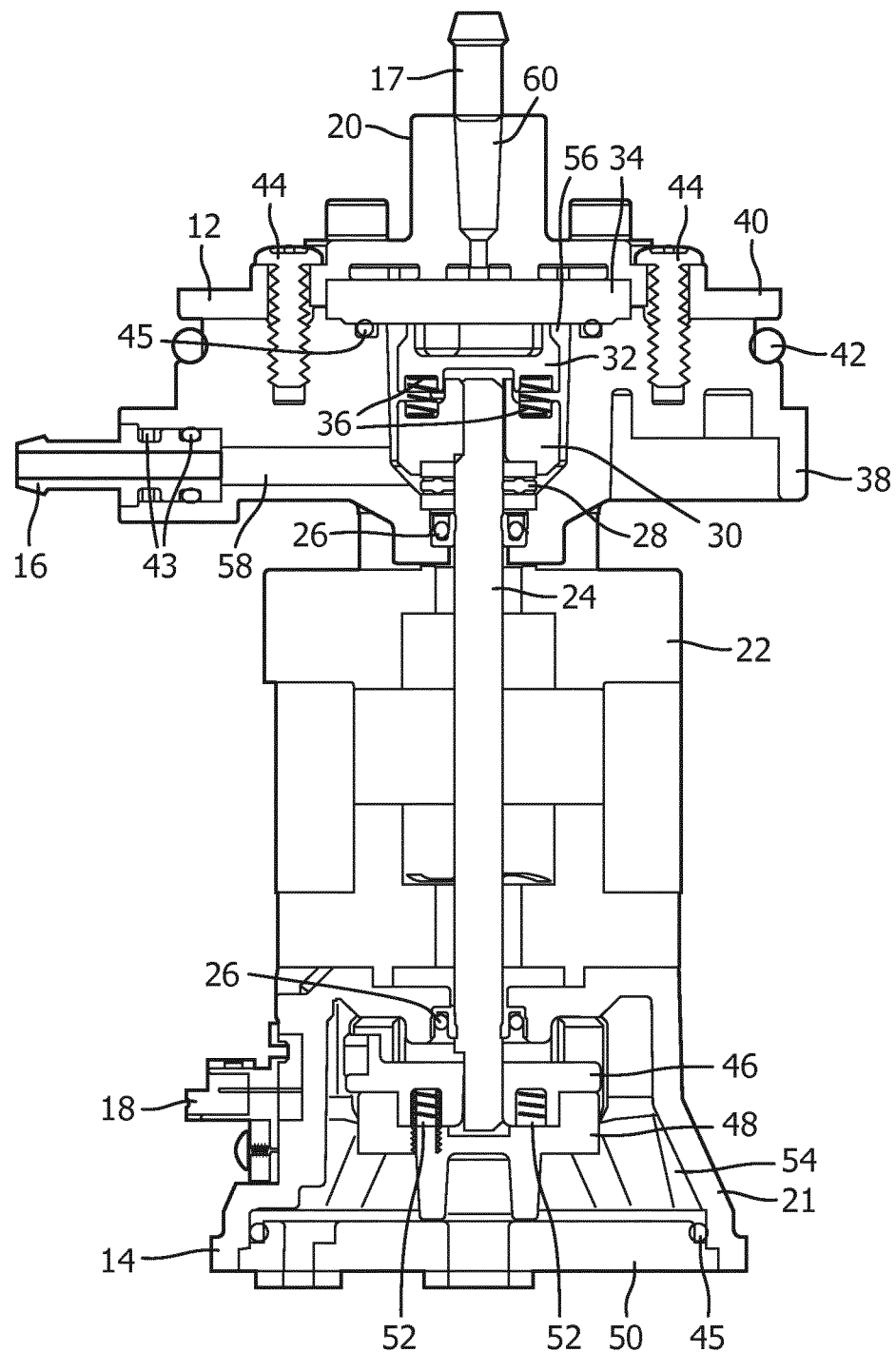
FIG. 3 is a sectional view of the rotary control valve taken along line 3-3 in FIG. 1.
Figure 4:
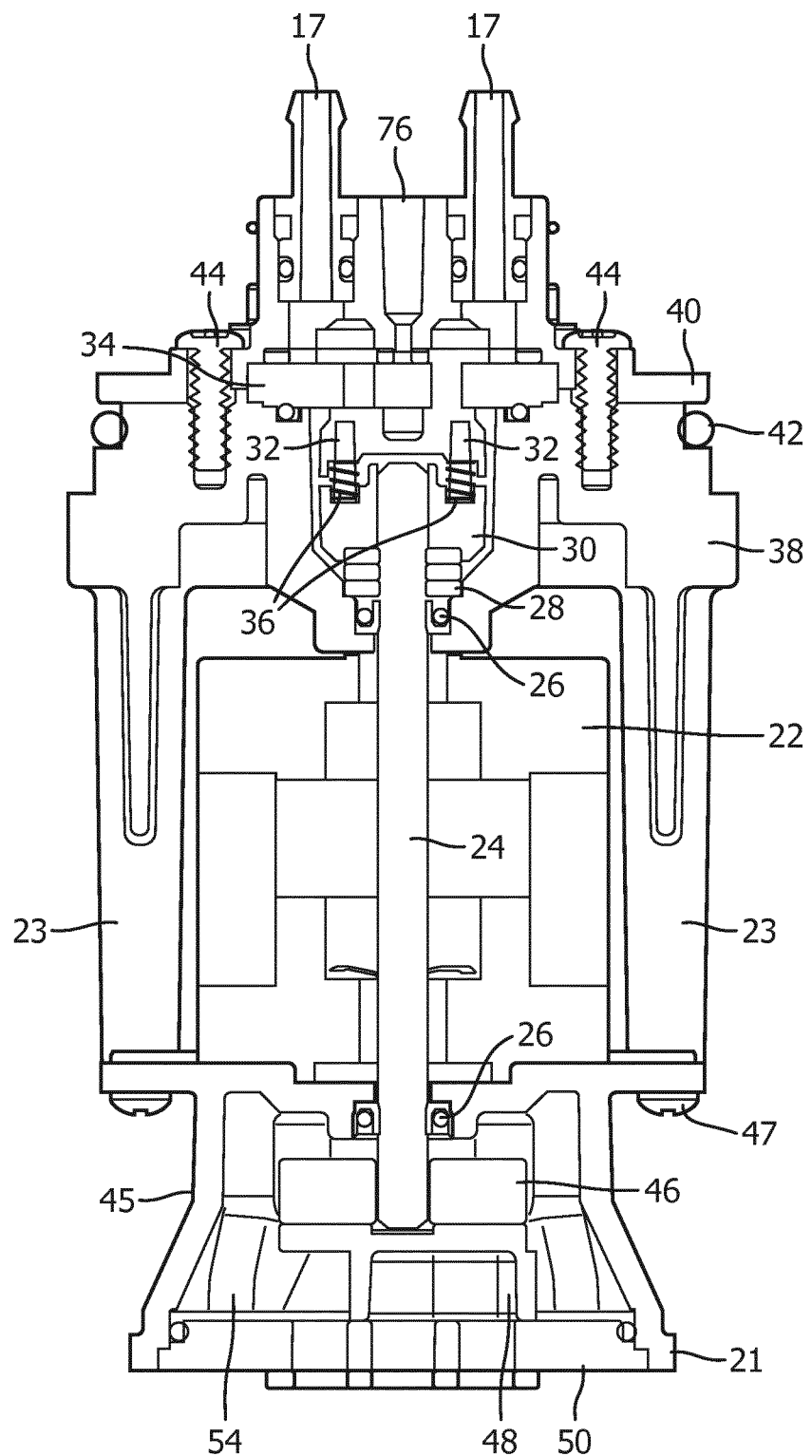
FIG. 4 is a sectional view of the rotary control valve taken along line 4-4 in FIG. 1.
Figure 5:
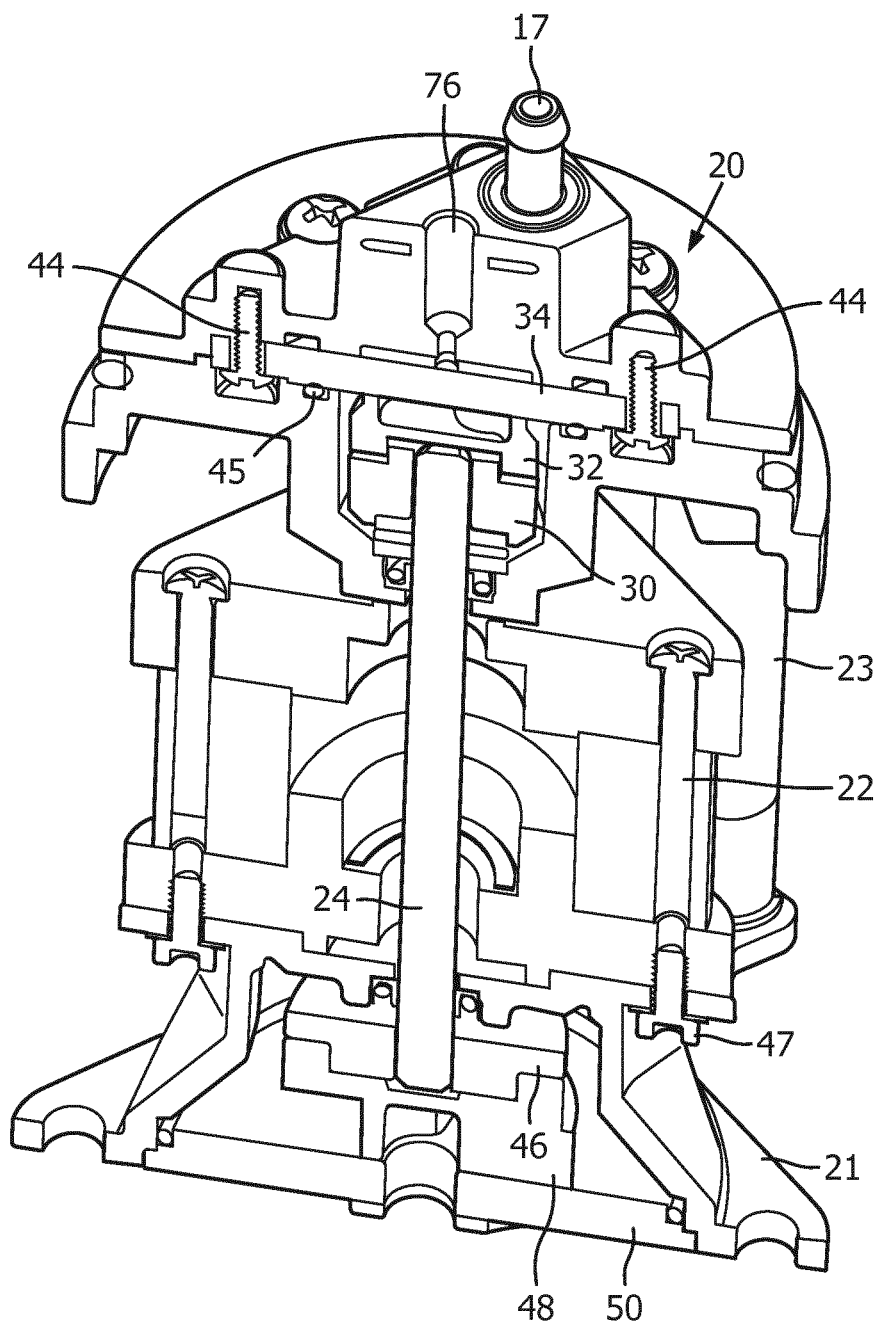
FIG. 5 is a sectional view of the rotary control valve taken along line 5-5 in FIG. 1.

The product end 12 of the rotary valve 10 is used to deliver product gas (e.g., oxygen) produced from sieve beds of an assembly. The product end 12 of the rotary control valve 10 includes a housing 20 provided at a top end that contains an internal product valve therein. The housing 20 includes a bottom part 38 and a top part 40. The bottom and top parts 38, 40 are secured together using fasteners 44 (e.g., bolts), placed through aligned openings, and enclose internal components of the product end 12 therein. The positioning or direction of insertion of the fasteners is not limited (e.g., see FIGS. 4 and 5). The internal components in the product end 12 include a product rotor 32 and a product stator 34, as seen in FIGS. 3 and 4, for example. The product rotor 32 and product stator 34 are contained within a chamber 56 or opening formed between a bottom part 38 and a top part 40 of the housing 20. The chamber 56 may hold pressurized gas (O2) therein for delivery to a patient (via a delivery system). The bottom part 38 of the housing 20 includes a delivery channel 58 that communicates the pressurized gas to the connector 16, for delivery or feeding of gas (O2) out of the valve 10 and to the patient (e.g., via hose or tubing connected to connector 16). The top part 40 of the housing 20 includes connectors 17 for feeding product gas through delivery channels 60 and into the chamber 56. As shown and described later, the connectors 17 may have tubing connected thereto for delivery of the product gas (oxygen) from sieve beds within a module assembly 100. Also, in an embodiment, the rotary control valve 10 also includes an orifice 76 or opening for communicating product gas from a product tank (e.g., see tank 106 in FIG. 18) into the chamber 56. As seen in FIG. 4, the top part 40 of the housing may include the orifice 76 therein for providing fluid communication directly with product storage tank 106.

Figure 22:
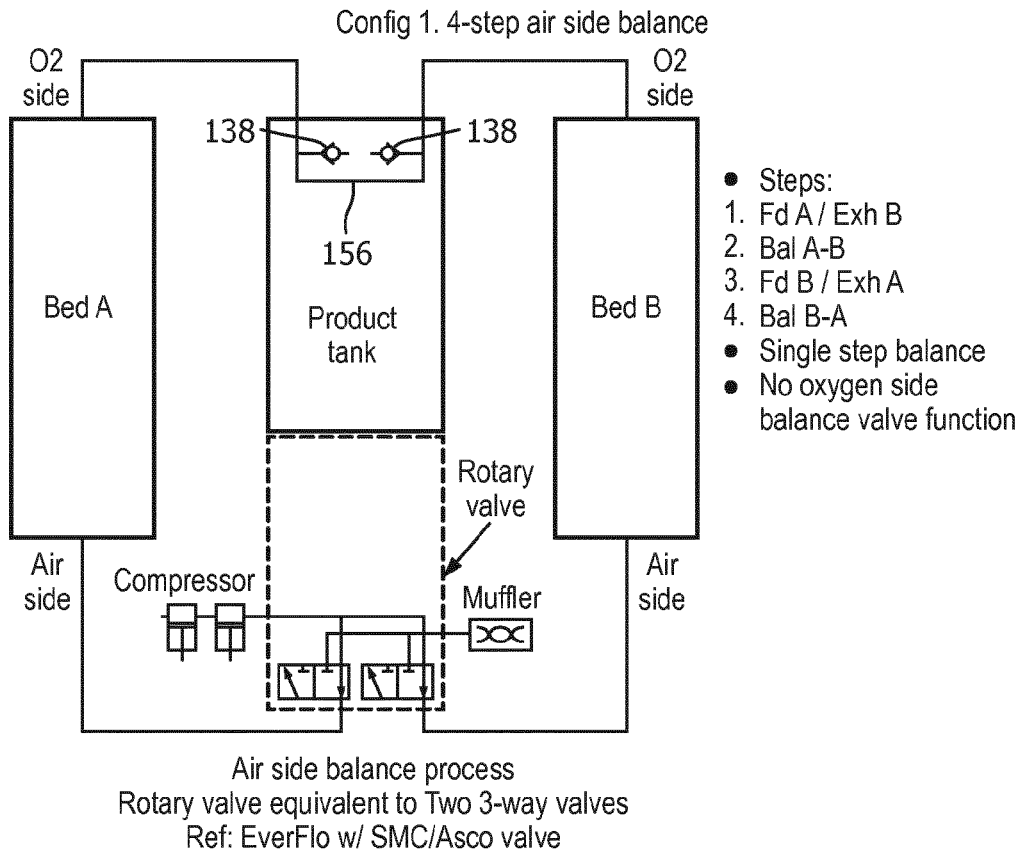
FIG. 22 illustrates a schematic diagram of valves replaced by the disclosed rotary control valve for a 4-step air side PSA process in the disclosed assembly, in accordance with an embodiment.

The air end 14 of the valve 10 feeds air to sieve bed(s) of the assembly (which produces the output product gas (O₂) for delivery to a patient) and/or exhausts the sieve bed(s). The air end 14 of the rotary control valve 10 also includes a housing 21 provided at a bottom end of the valve 10 that also contains internal components therein. The internal components in the air end 14 include an air rotor 48 and an air stator 50, also shown in FIGS. 3 and 4, which form an air delivery valve. The air rotor 48 is contained within a chamber 54 or opening within the housing 21. The air stator 50 encloses the air rotor 48 within the chamber 54. The chamber 54 may hold pressurized air therein. As schematically shown in FIG. 22, for example, the rotary valve 10 is operatively connected to a compressor 80 and a muffler 82. The compressor 80 is configured to compress atmospheric air and provide the compressed air as a source of feed gas to the chamber 54 of valve 10. Pressurized air may be delivered from the chamber 54 to one or more sieve beds based on the relative position of the rotor and stator 48, 50. Air may also be exhausted from the sieve beds and/or housing 21 via movement of the rotor 48 via muffler 82. The configuration and use of the compressor 80 and muffler 82 within an oxygen concentrator is generally known, and thus not described in detail herein.

The rotors 32, 48 are discs that are operatively connected or coupled to the shaft 24. The rotors 32, 48 are configured to simultaneously rotate with the shaft 24 of the motor 22 about the axis. The rotors 32, 48 include cavities therein that may align with one or more of ports of the stators 34, 50 during steps of a control process. As the rotors 32, 48 rotate, ports of the stationary stators 34, 50 may be exposed (e.g., to feed air), covered (partially or fully, to close a port), or connect a port to a center portion (e.g., open to exhaust, or open to product gas from a tank).

Figure 6:
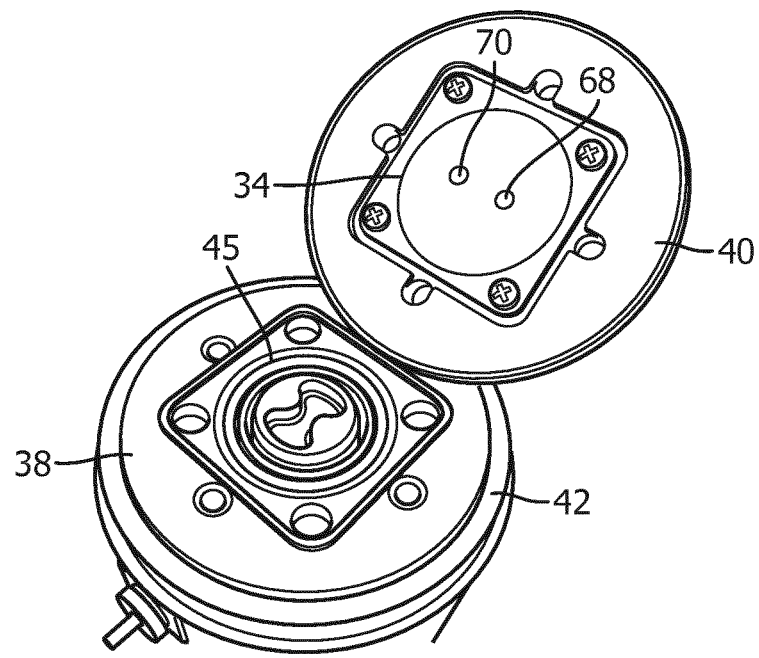
FIG. 6 is a top view of a housing of the rotary control valve of FIG. 1 being partially removed on a first side, showing a product stator and a product rotor, in accordance with an embodiment
Figure 9:
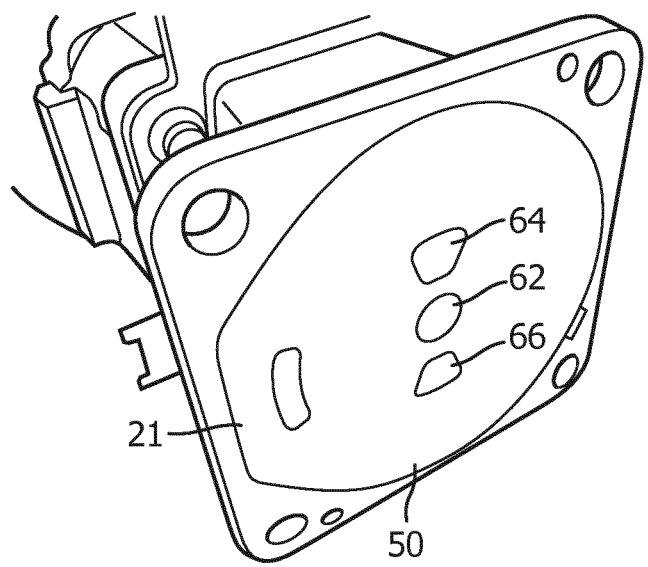
FIG. 9 shows a bottom view of the rotary control valve, with the air rotor and air stator assembled therein.

In an embodiment, each of the stators 34, 50 is provided in the form of a stationary plate at each end 12, 14 of the rotary control valve 10 that contain ports therein that lead to control nodes of an assembly (such as a module assembly 100, described with respect to FIGS. 11-19). For example, the plates may enclose the rotors 32, 48 within the chambers 56, 54 of the housings 20, 21 (respectively). In one embodiment, the air stator 50 has three ports in a line, an example of which is shown in FIG. 9. The center port 60 is an exhaust port that connects to and communicates with an exhaust portion of the system (e.g., see ports 112 and 116 in manifold 110, shown in FIGS. 14 and 16). The right and left ports 64, 66 on either side of the center port 60 lead to relative feed ends of the sieve beds in the module assembly 100. In an embodiment, the product stator 34 has two ports 68, 70, such as shown in FIG. 6. The two ports 68, 70 lead to the oxygen end of the sieve beds. In another embodiment, the product stator 34 has three ports, i.e., a center port is added in addition to the ports 68, 70. The center port may lead directly to a product (oxygen) storage tank (e.g., see tank 106 in FIG. 18).

Figure 7:
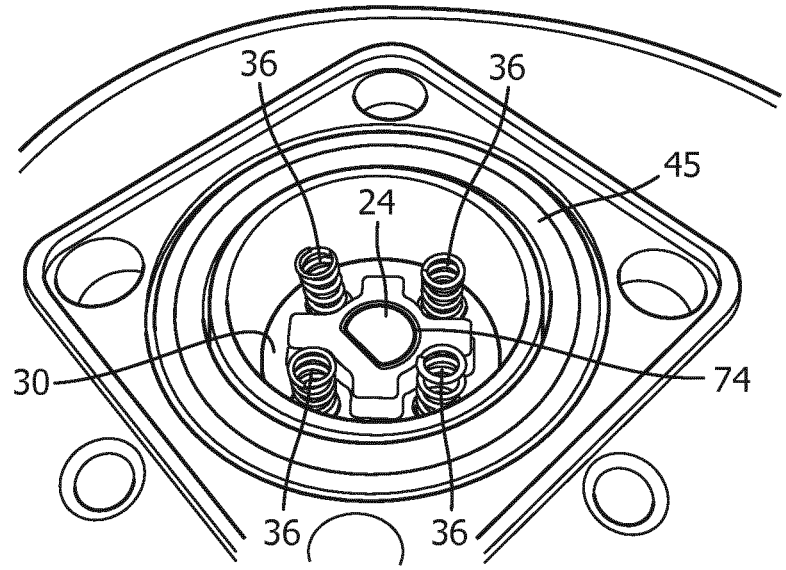
FIG. 7 shows a detailed view of a driver and springs in the housing of the rotary control valve on the first side as shown in FIG. 6, with the product rotor removed, in accordance with an embodiment.

The rotors are operatively connected to the shaft 24 of the motor 22 via drivers 30 and 46 for axial rotation. Specifically, in one embodiment, a product driver 30 is mounted to an end of the shaft 24 at the product end 12 and is operatively connected to the product rotor 32. An air driver 46 is mounted to an opposite end of the shaft 24 at the air end 14 and operatively connected to the air rotor 48. In an embodiment, the shaft 24 engages a connecting portion of each driver 30, 46. In another embodiment, the shaft 24 extends through a central opening provided within each driver 30, 46. The central opening of the driver and the shaft may have corresponding shapes, such that the driver and shaft may be press-fit together, for example. FIG. 7 shows an example of the top end of the shaft 24 being press fit into an opening 74 of the driver 30 at the product end 12, wherein the opening 74 has a shape that corresponds to the shape of the shaft 24 (e.g., a D-shaped shaft).

Each rotor and stator has a first side and a second side. The first side of the stator faces its respective housing, while the second side of the stator faces its respective rotor. A first side of each rotor faces its stator, while a second side (or underside) of the rotor faces its driver. In accordance with an embodiment, the second side of each rotor that faces its driver may have a mating surface that corresponds to a connective mating surface of its driver. The shaft 24 rotates the drivers 30, 46, which in turn rotate the rotors 32, 48. As the shaft 24 is rotated about its axis A, the product rotor 32 and the air rotor 48 are correspondingly moved about axis A.

The rotation of the shaft 24 is perpendicular to the sides (or faces) of the rotors. The rotors 32, 48 rotate relative to their respective stators 34, 50. As they rotate, the cavities within the rotors 32, 48 selectively align with the ports in the respective stators 34, 50, to achieve the desired valve function. Alignment of the cavities and ports in the rotary control valve 10 allows flow to or from the fluidly connected sieve beds, for example.

Figure 8:
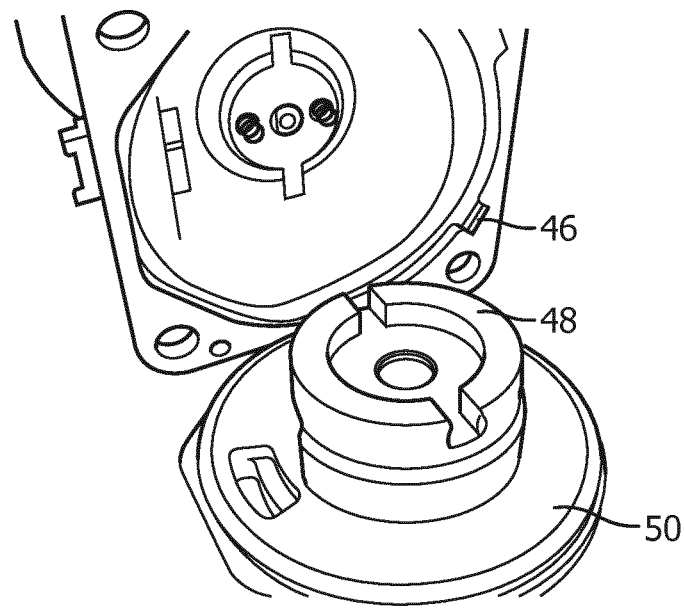
FIG. 8 is a bottom view of a housing of the rotary control valve of FIG. 1 on a second side, showing an air stator and an air rotor removed from the housing and a driver and springs in the housing, in accordance with an embodiment.

To maintain engagement of the rotors and stators at each end 12, 14 of the rotary control valve, a combination of biasing force and pressure may be used. As shown in FIG. 3, for example, biasing mechanisms 36 and 52 are provided between the drivers 30, 46 and the rotors 32, 48 (respectively) for biasing and sealingly engaging the rotors 32, 48 towards their respective stators 34, 50. The force applied by the biasing mechanisms 36 and 52 is designed such that it is greater than an opposing force and/or weight applied to the rotors 32, 48. In one embodiment, the biasing mechanisms 36, 52 are in the form of coiled compression springs. FIG. 7 shows an example of four (4) coil springs placed relative to the driver 30 that are designed to force rotor 32 upwardly towards and against the stator 34 when assembled in the housing 20. Optionally, oxygen pressure formed within the chamber 56 of housing 20 may also assist in holding the rotor 32 against the stator 34. FIG. 8 shows an example of two (2) coil springs placed relative to the driver 46 that are designed to force rotor 48 downwardly towards stator 50 when assembled in the housing 21. Pressurized air contained within chamber 54 may also provide pressure around air rotor 48 to assist with pushing the rotor 48 downwardly against the stator 50.

A shaft seal on one or both ends of the rotary control valve 10 may be included to prevent or diminish any leakage that can occur between the motor shaft 24 and surrounding housing(s) 20 and 21. For example, as shown in FIG. 3, seal bearings 26 may be provided around the shaft 24 within a bottom part 38 of housing 20 and within housing 21. In cases where the thrust load on the product side 12 of the valve exceeds the capacity of the stepping motor 22, a thrust bearing 28 (also shown in FIG. 3) can be added to absorb this load, and protect the motor 22.

Figure 18:
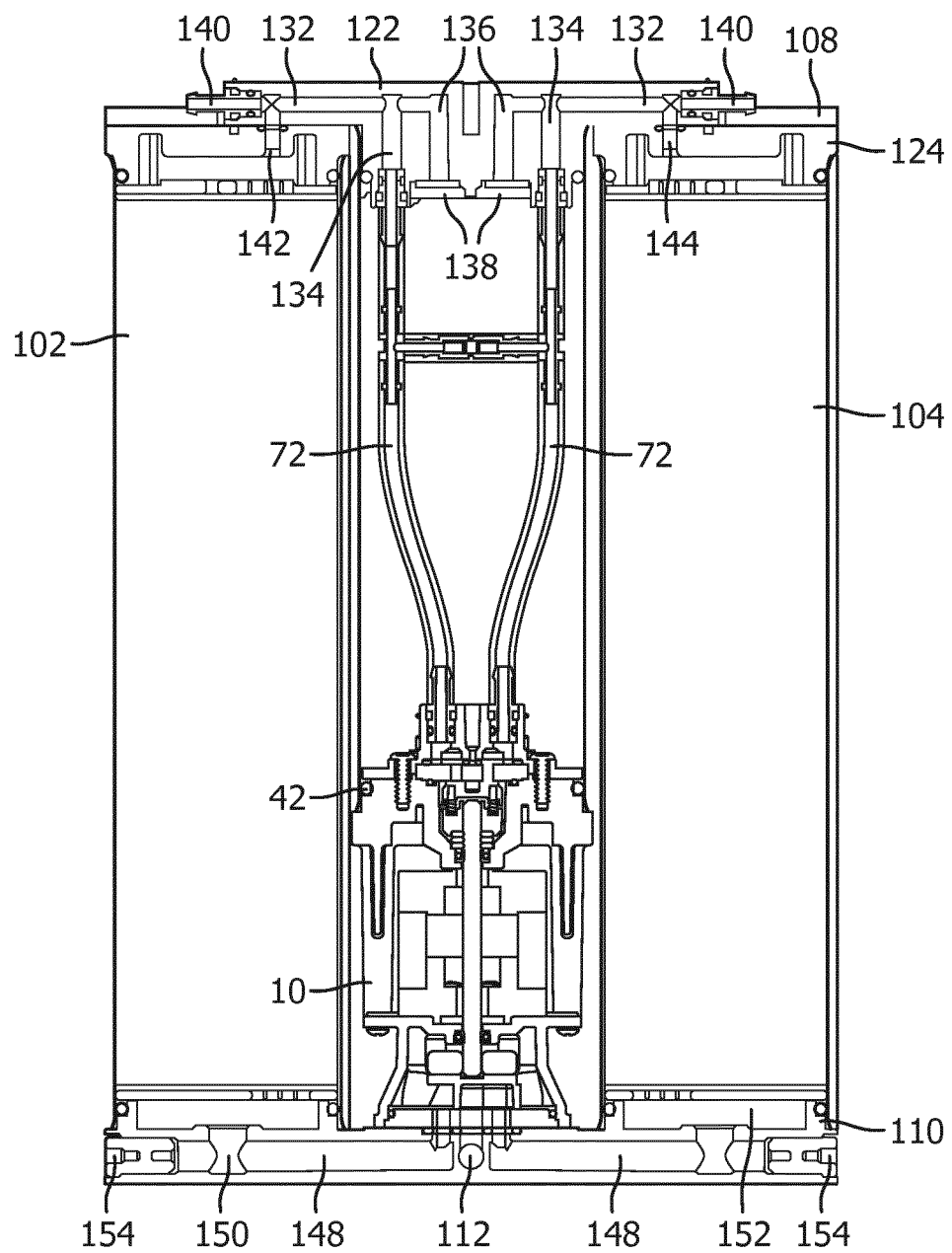
FIG. 18 is a sectional view of the module assembly taken along line 18-18 in FIG. 11.

One or more O-rings or seals may be provided in and around the rotary control valve 10. For example, an O-ring 42 is provided around housing 20 to sealingly engage the valve 10 within a product storage tank 106 of a module assembly 100, as seen in FIG. 18. O-rings 43 (see FIG. 3) may be provided around connector 16 to sealing engage the connector within an opening of the housing 20 (in the bottom part 38) for alignment with the delivery channel 58. One or more O-rings 45 may also be provided between the stators 34, 50 and housings 20, 21 to sealingly secure the chambers 56, 54.

The motor 22 is provided between the product end 12 and the air end 14 of the rotary control valve 10. The motor 22 drives the shaft 24 about the vertical axis A for axial rotation either in a clockwise or counterclockwise direction. As shown in FIG. 3, for example, the shaft 24 extends through the motor 22 and beyond the ends of the motor 22 in both directions. In an embodiment, bearings 26 (and/or 28) and drivers 30, 46 are provided on the ends of the shaft 24, outside and adjacent to ends of the motor 22. As shown in FIG. 1, the motor 22 is surrounded by support posts 23. The support posts 23 extend between and are attached to the housings 20, 21. The posts 23 are used to secure the housings 20, 21 together with the motor 22 therebetween to form assembly. The posts 23 assist in providing structural rigidity to the assembly. In an embodiment, the length of the posts 23 is consistent with the height of the motor 22. The posts 23 are releasably connected at either end to a part of the housings 20 and 21. For example, as shown in FIG. 4, in one embodiment, the posts 23 may connect to housing 20 via receipt of an extension portion of housing 20 therein (e.g., within a center of each post), while fasteners 47 are used to secure the opposite end of the posts 23 to a lip of the housing 21. The tightening of the fasteners 47 secures the housings 20, 21 together thus assuring that housing 20 does not rotate relative to housing 21.

In accordance with an embodiment, the motor 22 is a controllable or programmable stepper motor, controlled by a controller (not shown). The controller may accelerate or decelerate the motor in a negligible or short amount of time. The stepper motor 22 may be a hybrid motor having a single, double, or triple stack. In one embodiment, the stepper motor 22 may be a NEMA 17 size stepper motor (~42 mm square)×30 mm-42 mm in length, and have 200 steps per revolution.

The motor 22 is configured to rotate the shaft 24 through a 360 degree cycle and configured to stop rotation of the shaft 24 and dwell for a period of time at a number of positions or steps about the 360 degree rotation. Such cycles are also referred to as "PSA processes", examples of which are described later.

Figure 10:
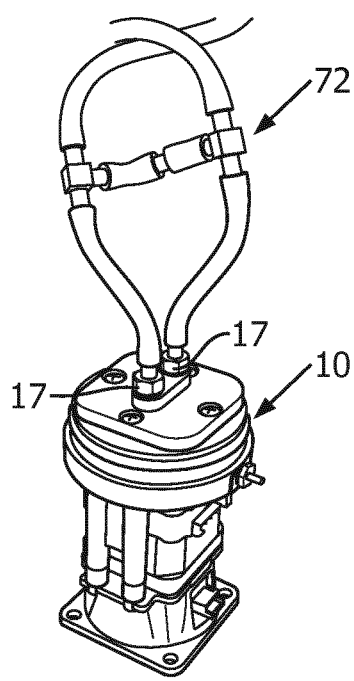
FIG. 10 shows the rotary control valve of FIG. 1 having tubing attached thereto.

The connectors 17 in the top part 40 of the housing 20 of the rotary control valve 10 are used to receive produced product gas (O2) from a sieve bed. As shown in FIG. 10, the connectors 17 have one end of a piece of tubing 72 connected thereto. The other end of the tubing is configured for connection to a delivery port 128 within the module assembly 100 for delivery of the product gas from one or more sieve beds of the assembly. FIGS. 11-19 illustrates features of an exemplary module assembly 100 configured to employ the rotary control valve 10 therein. The assembly 100 acts as an air separation device (i.e., capable of separating oxygen from air) using pressure swing adsorption technology. As shown, the disclosed design of the module assembly 100 integrates two molecular sieve beds 102, 104, a product storage tank 106, and the rotary control valve 10 into a compact, flexible, and scalable module. The molecular sieve beds 102, 104 are provided in the form of columns that include active molecular sieves therein which are designed to adsorb nitrogen from intake air and produce oxygen-rich gas. The input to the sieve beds 102, 104 of the assembly 100 is compressed air, and the output is enriched (e.g., 86-96%) oxygen product gas, which may be delivered to a patient. Depending on the amount of air input and the characteristics and size of the sieve beds and valve ports, the output can vary from 3 LPM to 10 LPM of product gas. In one embodiment, the output is rated for 5 LPM oxygen output.

It should be noted that, although the module assembly 100 as disclosed herein is described as employing the rotary valve 10, other configurations of valves may be used with the module assembly 100. That is, the type and design of control valve(s) used with module assembly 100 is not intended to be limited. In accordance with an embodiment, one or more valves may be provided in the module assembly 100 (e.g., such as known solenoid valves, two-way valves, and/or three-way valves).

Figure 14:
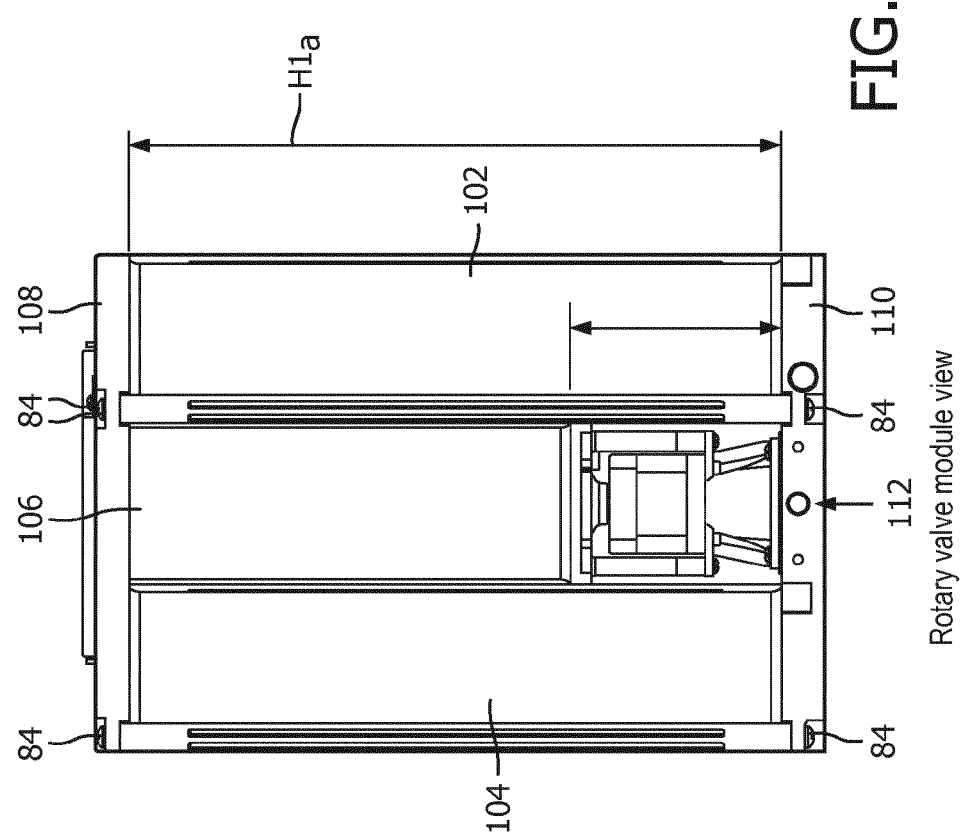

As shown in FIG. 12 and FIG. 14, for example, the columns of the two sieve beds 102 and 104 (also referred to herein as "Bed A" and "Bed B," respectively) flank the rotary control valve 10 (or other control valve(s)) in the assembly 100. For explanatory purposes only, the module assembly 100 is shown and described below as using the disclosed rotary control valve 10. The rotary control valve 10 assists in fluid flow between sieve beds 102, 104 for feeding the beds, equalizing or balancing the beds, purging the beds, etc. during a selected PSA process. More specifically, the air end 14 of the valve 10 both delivers air to the sieve bed(s) 102, 104 and exhausts air from the sieve beds 12, 104, as needed, while the product end 12 is used to deliver product gas (oxygen) from the product storage tank 106 (received via the sieve beds 102, 104) to the patient.

The rotary control valve 10 is positioned under the product storage tank 106 (see FIGS. 12 and 14) to facilitate air and oxygen side control. The product storage tank 106 stores the gas produced by the sieve beds, or "product gas" e.g., purified oxygen gas. The product storage tank 106 is secured in between the sieve beds 102, 104. In a non-limiting embodiment, the product storage tank 106 is centered between the sieve beds 102, 104, such that the centers of the tank and beds are linearly aligned (see FIG. 11). In another embodiment, the centers of the tank and beds are provided in a triangular configuration (see description with regards to FIGS. 20 and 21). Despite the configuration, the product tank 106 is positioned above the rotary control valve 10. More specifically, the product storage tank 106 is linearly aligned with (in a vertical direction) and placed above the rotary control valve 10 to form a stacked configuration.

Figure 17:
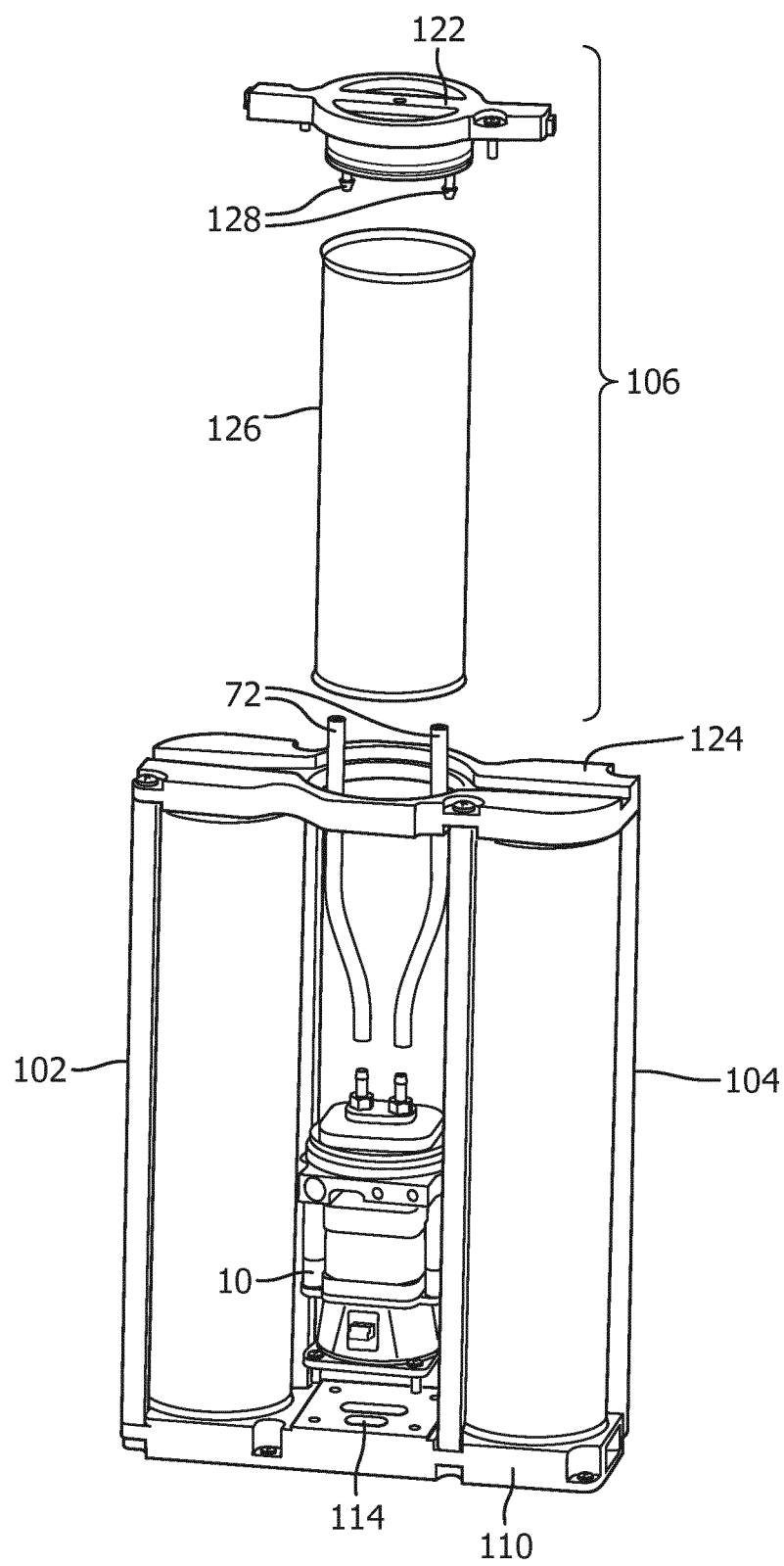
FIG. 17 is an exploded view of the parts of the module assembly of FIG. 11.
Figure 19:
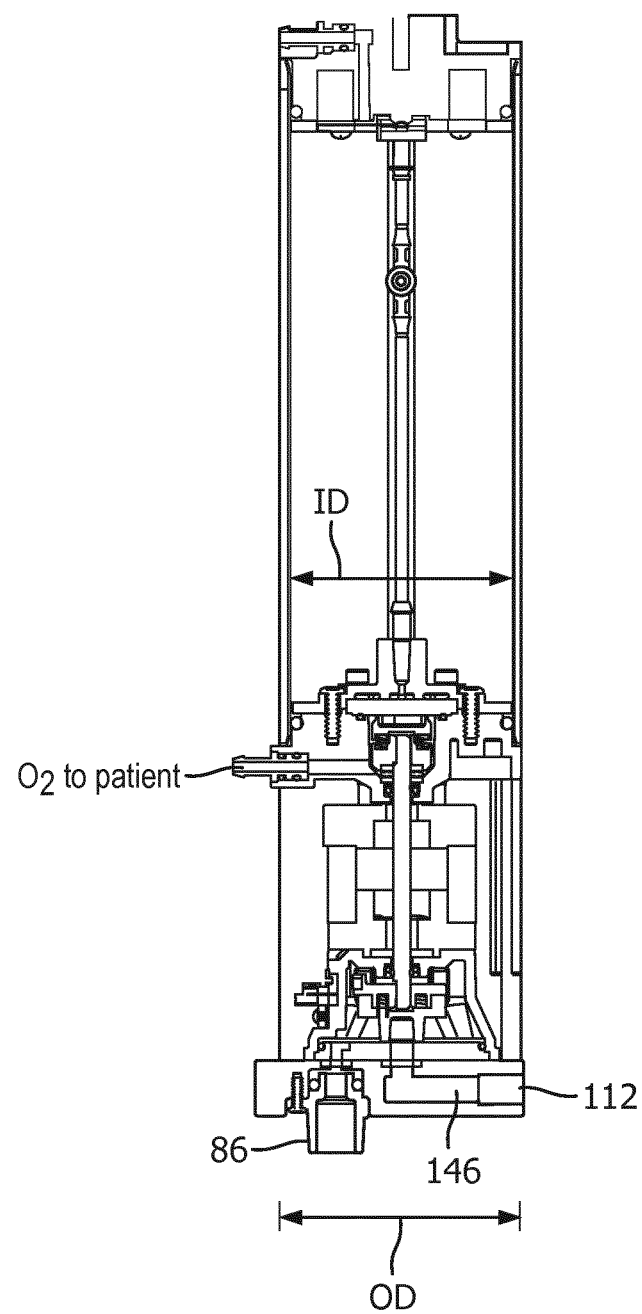
FIG. 19 is a sectional view of the module assembly taken along line 19-19 in FIG. 11.

FIGS. 17, 18 and 19 illustrate the assembly of the product storage tank 106 and the rotary control valve 10 in greater detail. The product tank is formed from the assembly of a first part 122 of an upper manifold 108 and tube 126 with the rotary valve 10, as shown in FIG. 17. In an embodiment, an outer diameter OD of the rotary control valve 10 (e.g., outer diameter of housing 20)(see FIG. 19) is of the same or less dimension as an inner diameter ID of the tube 126 of the product storage tank 106. This allows for axial alignment of the valve 10 and the tank 106 (e.g., centers are aligned along axis A), and so that tube 126 may be coupled to the housing of the rotary valve 10. More specifically, in the assembly, the tube 126 of the product storage tank 106 surrounds the top part 40 of the housing 20 at the product end 12 of the valve 10 (see FIGS. 18 and 19). In one embodiment, the tube 126 also extends around at least a portion of the bottom part 38 of the housing 20. The O-ring 42 is provided between an outer wall of the housing 20 and inner wall of the tube 126. Accordingly, the product/oxygen side valve function is directly coupled to the storage tank 106. Further, as seen in FIG. 18, for example, the product rotor 32 and product stator 34 of the internal components on the product side 12 are substantially enclosed and provided within the product storage tank 106.

Placement of these valve components within the product storage tank 106 (and inside the sieve module envelope)—as opposed to valve placement outside of the sieve module envelope, as in prior art systems—provides easier mounting and connection of the valve 10 with the sieve beds 102, 104. Moreover, multiple gas connections between multiple valves above, below, and/or to side of the sieve bed columns is reduced, and any size, weight and complexity issues because of multiple valve connections is decreased.

The above-described configuration (stacked tank 106 and valve 10 that is secured together via O-ring 42) also greatly reduces and/or eliminates any pressure leakage from the product storage tank 106. This provides a significant cost reduction, since leakage is common in prior art designs and product gas (like O2) can be expensive to purchase and canister. Furthermore, if there is a leak of product gas in the disclosed configuration, the leak is designed for delivery into one or more parts of the module assembly 100, and thus can still be used for oxygen therapy.

Figure 11:
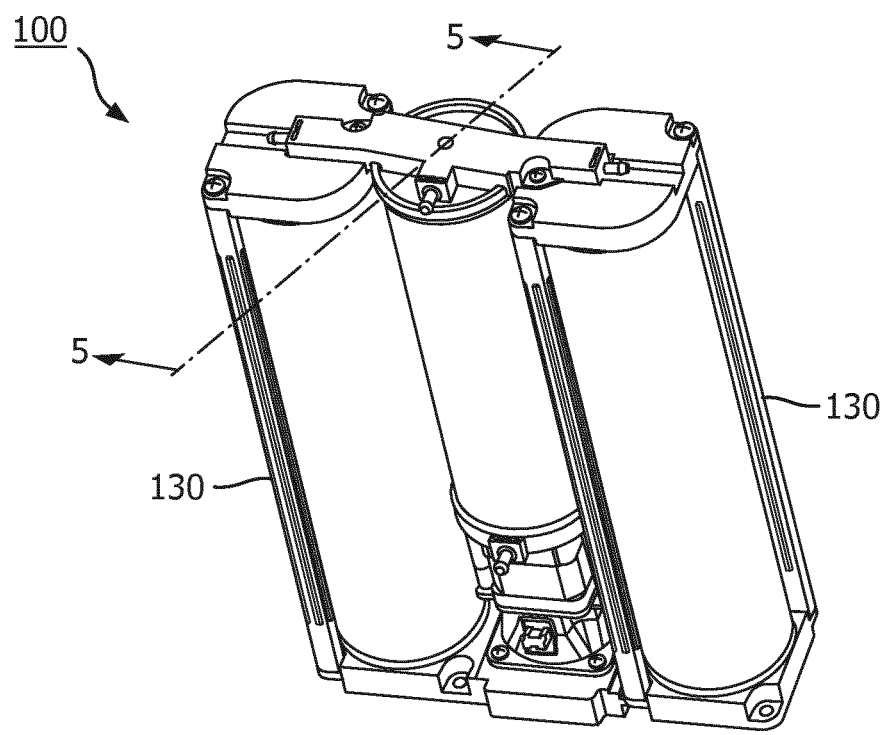
FIG. 11 shows the rotary control valve of FIG. 1 assembled in a module assembly in accordance with an embodiment.
Figure 15:
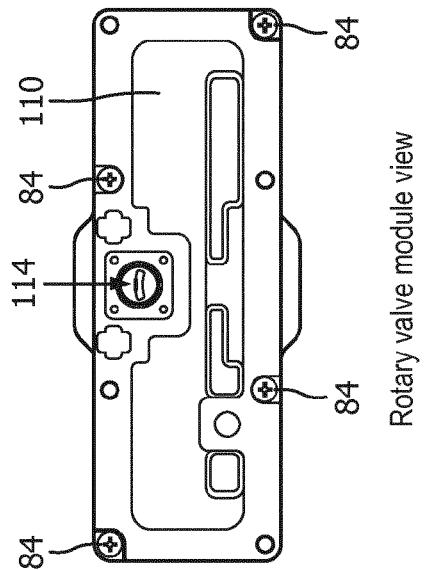

To secure the molecular sieve beds 102, 104, a product storage tank 106, and the rotary control valve 10 into their compact configurations, manifolds 108, 110 may be used. An upper manifold 108 is provided on the product/oxygen side of the sieve beds 102, 104, as seen in FIG. 11 (on top of the assembly 100). A lower manifold 110 is provided relative to the air side 14 of the rotary control valve 10. In one embodiment, a top of each of the columns of the sieve beds 102 and 104 and a top of the tube 126 of the product storage tank 106 is secured to the upper manifold 108. A bottom of each of the columns of the sieve beds 102 and 104 and a bottom of the rotary control valve 10 is secured to the lower manifold 110. The rotary control valve 10 may be secured in a center of the lower manifold 110, with Bed A/sieve bed 102 secured to the manifold 110 on a left side of the valve 10, and Bed B/sieve bed 104 secured to the manifold 110 on a right side of the valve 10 (see FIG. 12). The product tank 106 is secured on top of the rotary valve 10 and in between the beds 102, 104. In accordance with an embodiment, the top and bottom manifolds may be in the form of plates.

FIG. 17 shows one exemplary embodiment wherein the upper manifold 108 includes two parts—a first part 122 and a second part 124—that connect and secure the product storage tank 106 and sieve beds 102, 104 together in the assembly 100. As shown in FIG. 18, the first part 122 of manifold 108 includes a plurality of channels 132-136 therein for fluidly connecting the product storage tank 106 with the sieve beds 102, 104. The channels 132-136 receive product gas from the sieve beds 102, 104 via orifices 142, 144. Specifically, the second part 124 includes orifice 142 for fluid communication with sieve bed A 102 and orifice 144 for fluid communication with sieve bed B 104. The orifices 142, 144 may be openings with o-ring seals therein, for example. Each of the orifices 142, 144 connects to a respective tunnel 132 provided within the first part 122. The tunnels 132 are secured via plugs 140 provided at their respective ends on either side of the manifold 108. Each tunnel 132 also has at least two channels 134, 136 branching off in a downward direction therefrom. Channel 134 includes a delivery port 128 (with optional connector therein) for delivery of the product gas to tubing 72 connected to the rotary valve 10. Channel 136 connects to a one-way valve 138, e.g., a flapper valve, and feeds into the tube 126 of the product storage tank 106. The one-way valve 138 may made of rubber, for example, and designed to be forced open when pressurized product gas from one or more of the sieve bed(s) exceeds a specified amount, so that the product gas is fed into the tank 106. As such, the two-part manifold 108 as direct flow of product (oxygen) towards the product storage tank 106 and the product side 12 of the rotary control valve 10. The rotary valve 10 may receive product gas via delivery through tubing 72 and connectors 17 and/or via orifice 76.

As shown in FIGS. 17-19, in some embodiments, tubing 72 and flow control connectors 17 are contained within the tube 126 of the product storage tank 106. Thus, the tubing, fittings, and/or hoses are unexposed.

The lower manifold 110 also includes a number of ports and fluidly connected channels therein. As shown in FIG. 14, a back of the lower manifold 110 includes an exhaust port 112 for exhausting air from an internal tunnel 146 (see FIG. 19) connected to the sieve beds 102, 104. The exhaust port 112 may expel gas from either of the sieve beds 102, 104, e.g., through muffler 82, as a result of a pressure differential.

Figure 16:
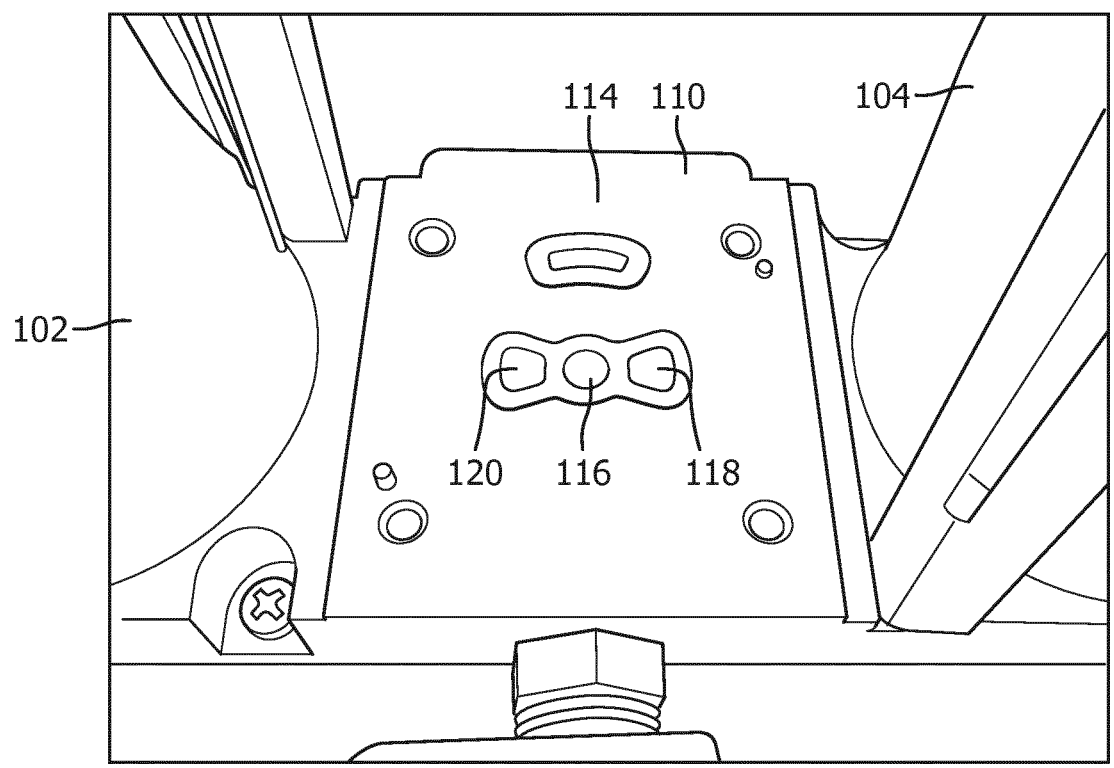
FIG. 16 shows a detailed view of a mounting surface in the module assembly for receiving the rotary control valve of FIG. 1, in accordance with an embodiment.

The internal tunnel 146 of lower manifold 110 may also be used to deliver air to the sieve beds 102, 104. The lower manifold 110 has an inlet port 114 for delivery of pressurized air from the compressor 80 to the rotary control valve 10. Thus, the compressor 80 provides compressed air as a source of feed gas to a sieve bed on its feed side via the lower manifold 110. The inlet port 114 extends between a bottom surface (see opening in FIG. 15) and a top surface (see opening in FIG. 16) of the lower manifold 110. Optionally, in one embodiment, a fitting 86 (see FIG. 19) is provided within the inlet port 114 for connection to one or more parts of the compressor 80. As shown in FIG. 16, the lower manifold 110 includes a center port 116 and side ports 118 and 120 that are configured to be selectively in fluid communication with ports 62 and 64, 66 of the air stator 50 in the rotary control valve 10. When the air rotor 48 is rotated such that at least one of its cavities is at least partially aligned with one or more of ports of the stator 50, pressurized air may be directed to one or more of the sieve bed(s) 102, 104.

As shown in FIG. 18, the internal tunnel 146 includes side branches 148 for directing the air to the beds. The branches 148 extend from a center of the manifold 110 towards the sieve beds 102, 104 and outer ends of the manifold 110. Each branch 148 has an opening 150, 152 that is respectively aligned with sieve bed 102, 104 (e.g., port 150 is provided in a center of a sieve bed column) for delivering pressurized air. An outer end of each branch 148 includes a plug 154 therein.

In addition to reducing the number of valves, required gas connections, size, and weight required for typical assemblies or oxygen concentrators, the assembly of parts as described herein also assists in minimizing at least the longitudinal dimensions of the product storage tank 106 and the sieve beds 102, 104. As shown in FIG. 14, for example, sieve bed 102 (Bed A) has as height H1a and sieve bed 104 (Bed B) has a height H1b. In the illustrated embodiment, the sieve beds 102, 104 are of similar height, i.e., H1a is equal to H1b (Ha1=H1b). The rotary valve 10 has a height Hr and the product storage tank 106 has a height Hp. In accordance with an embodiment, the combined height of the valve 10 combined with the height of the product storage tank 106—i.e., Hr+Hp—is approximately equal to the height H1a or H1b of the sieve bed columns 102, 104. In one embodiment, the combined height of the valve 10 combined with the height of the product storage tank 106—i.e., Hr+Hp—is less than the height H1a or H1b of the sieve bed columns 102, 104.

The columns of the sieve beds 102, 104 also include an internal diameter. Sieve bed 102 (Bed A) has a diameter of D1, and sieve bed 104 (Bed B) has a diameter of D2, as shown in FIG. 12. In accordance with one embodiment, the diameters of the columns are substantially equal, i.e., D1 is equal to D2 (D1=D2). In an embodiment, the diameter ID of the product storage tank 106 is approximately equal to the diameters D1, D2 of the beds 102, 104. In another embodiment, the diameter ID of the product storage tank 106 is less than the diameters D1, D2.

In an embodiment, corner posts 130 (see FIGS. 12-14 and 17) are provided and secured between the upper manifold 108 and lower manifold 110 using fasteners 84. The corner posts 130 to provide greater stability to the assembled beds 102, 104, valve 10, and product storage tank 106 in the assembly 100. The corner posts 130 also aid in pneumatic sealing of the parts in the module assembly 100.

Figure 20:
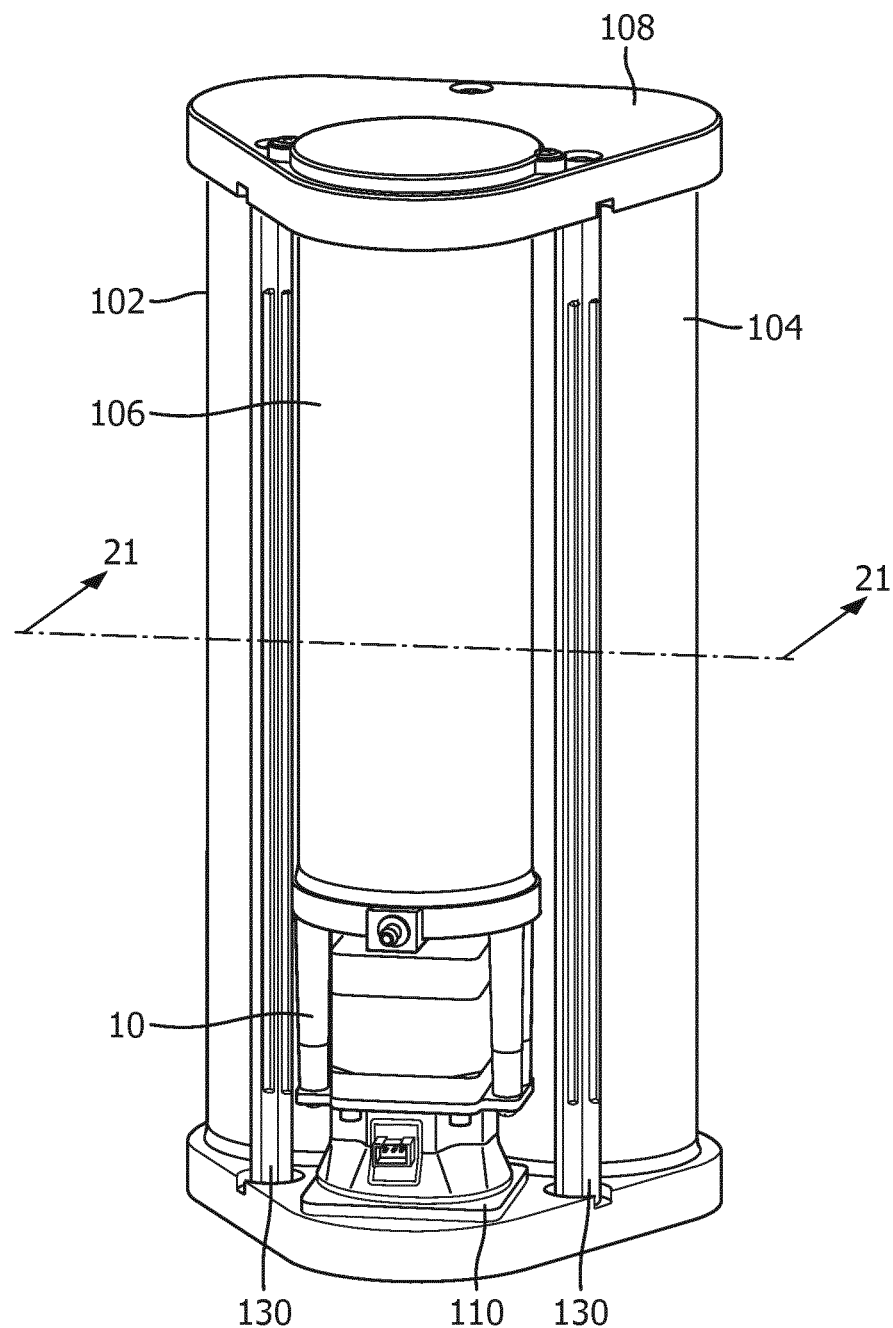
FIG. 20 shows the rotary control valve of FIG. 1 assembled in the module assembly in accordance with another embodiment.
Figure 21:
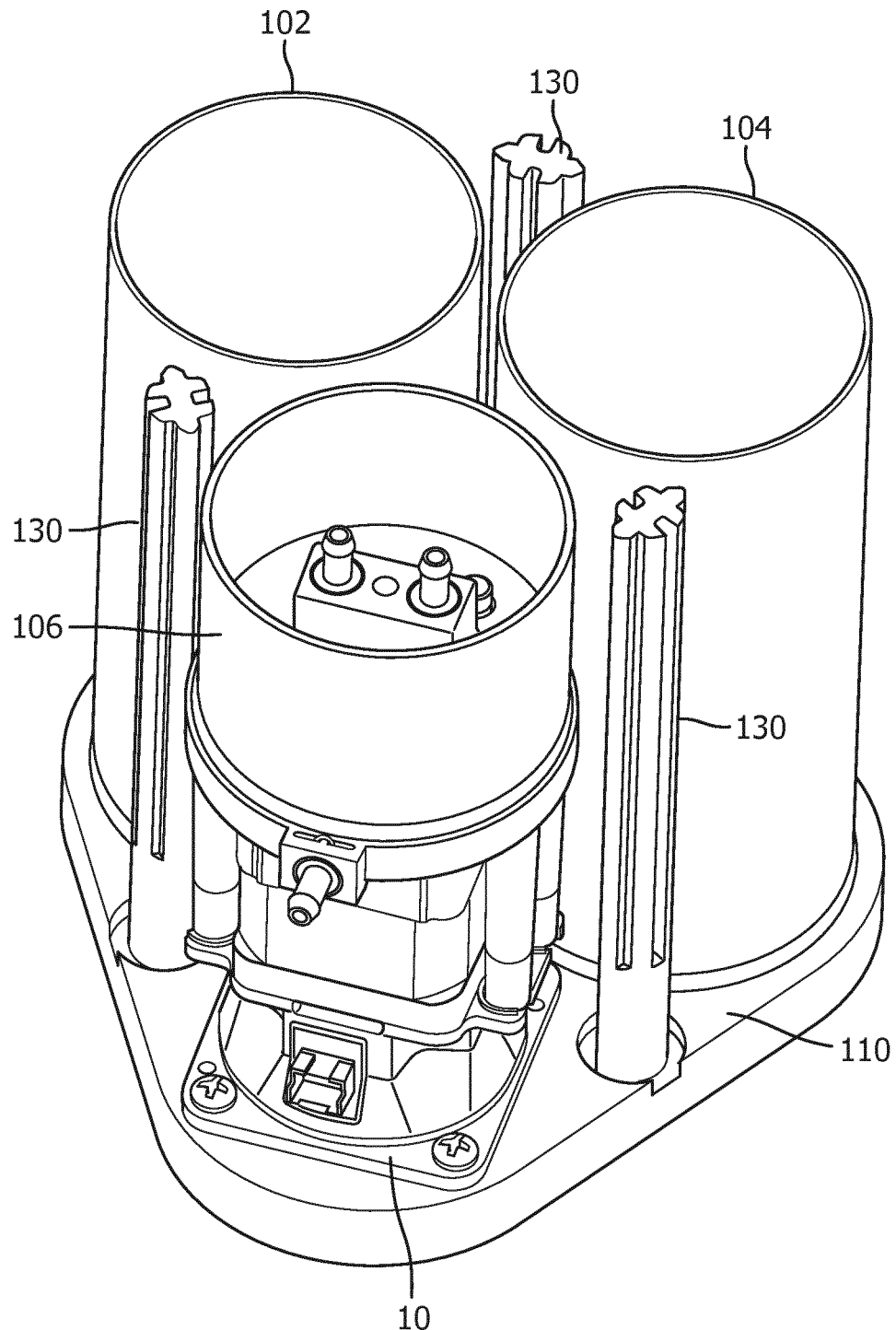
FIG. 21 is a sectional view of the module assembly taken along line 21-21 in FIG. 21.

In the embodiment described above with reference to FIGS. 17-19, the sieve beds 102, 104 and product storage tank 106 utilize tubes in a linear geometry (Sieve Bed A—product storage tank—Sieve Bed B), which minimizes the depth dimension. As previously noted, in an alternate embodiment, the columns of the sieve beds 102, 104, product storage tank 106, and rotary valve 10 are configured in an equilateral triangular arrangement, which is shown in FIGS. 20 and 21. In this triangular arrangement, the width and depth dimensions are approximately equal. In yet another embodiment, the tubes of the sieve beds and product storage tank can be configured in a "L" or "Z" pattern, with each sieve bed 90 degrees off axis relative to the product storage tank (not shown). Despite the configuration, with the rotary control valve 10 and the product 106 being positioned as previously described (e.g., in a stacked configuration and having a combined height substantially equal to or less than the height of the sieve beds), equally and "in between" the two sieve beds, the advantages and functionality of the module assembly 100 is maintained.

Accordingly, the height dimensions of the beds and tank, in combination with the previously mentioned dimensions and configurations of the product storage tank 106 and rotary valve 10, ensure a compact module. Further, in accordance with an embodiment, the overall dimensions (depth and height) of the product tank 106 and valve 10 are not greater than the combined dimensions (e.g., diameter and height (length)) of the sieve bed columns. The integration of the valve, sieve bed, and product buffer tank in this manner, results in a small, compact, lightweight oxygen generation module. The module assembly is scalable, and limited only by component availability.

Known assemblies tend to implement one particular gas separation process, with variables such as the time spent at each process step, and the number of steps. However, the disclosed rotary control valve 10 and module assembly 100 are not limited to a single separation process. Instead, in accordance with embodiments herein, different variations of the rotor (and (optionally) stator) components, along with a reprogramming of the controller for the motor 22, may be employed to affect different gas separation process controls, i.e., a different balance or PSA process (e.g., from a 4-step to a 6-step process). Removal and replacement of the rotary valve 10 can be easily performed without disassembly of the sieve beds 102, 104 from the top and bottom manifolds 108, 110. Referring to FIG. 17, disassembly may begin by simply disconnecting the columns 130 and the upper manifold plate 108 from the lower manifold plate 110. This allows the removal of the product storage tank 106 (e.g., removal of tube 126) and the tubing 72, which then enables removal of the rotary valve module 10 from the lower manifold 110.

In accordance with an embodiment, the entire rotary valve 10 is replaced within the module assembly 100 to change the PSA process. In another embodiment, the rotary valve 10 itself is disassembled to change the PSA process. For example, the housings 20, 21 may be unfastened and opened to replace the rotors 32, 48 (and optionally, the stators 34, 50) therein. The rotors 32, 48 may be provided in corresponding pairs such that they employ the selected process (e.g., for number of steps/step length and dwell time). The stators 34, 50 need not be changed. However, in some embodiments, one or both of the stators 34, 50 may be changed or swapped, e.g., depending on the selected process, or based on considerations such as motor output torque (motor torque capability versus size).

Accordingly, in one embodiment, the selected rotor/stator combinations and designs for the product side 12 and/or the air side 14 is dependent upon the step cycle to be employed using the rotary control valve 10. Generally, for each side, each of the rotors employed for a selected PSA process has a similar configuration. Using FIGS. 27 and 28 as an example, shown are first and second sides, respectively, of an air rotor 48 configured for use on the air side 14 of the valve 10 (in this case, in a 4-step DSB process). On the first side of the air rotor 48 in FIG. 27, there is a provided a receiving portion 88 flanked by walls 90. The receiving portion 88 receives an end the shaft 24 of motor 22, and walls 90 surround the end of the shaft 24.

Figure 42:
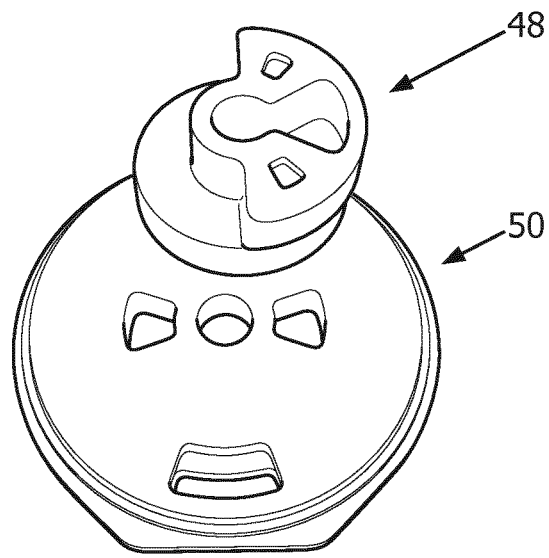
FIGS. 42-43 show examples of how the stator and rotor are mounted together when assembled in the rotary control valve on the second side.

Although two walls 90 are shown, any number of walls, including a single wall, may be provided on the first side of the rotor 48 to surround the shaft 94. Multiple cavities 92 (shown here as circular holes) are provided in an arc near one edge of the rotor 48. On the second side of the air rotor 48, as seen in FIG. 48, there is provided a first bell shaped depression 94. In one embodiment, a second depression 96 of corresponding shape is provided on the second side of the air rotor 48. FIG. 42 illustrates an alternate embodiment of a second side of an air rotor 48. This second side includes a protrusion on one side of the rotor 48, with the bell shaped depression 94 provided therein.

FIGS. 29-30 illustrate an example of first and second sides, respectively, of a product rotor 32 (also referred to as an "oxygen side rotor", below) configured for use on the product side 12 of the valve 10 (in this case, in a 4-step DSB process). The first side of product rotor 32 in FIG. 29 shows a connector 98 for connection to the product stator 50. In one embodiment, as shown in FIG. 29, the second side of the rotor 32 includes two kidney-shaped ports 78A that communicate with openings 78B (see FIG. 30) provided on the second side of the rotor 32. The ports 78A, 78B are configured to open or close communication between the sieve beds 102, 104 as it rotates between steps in a PSA process. The second side of the product rotor 30 has a receiving portion 88A, with surrounding extended walls 90A, for receipt of the opposite end of the shaft 24 of the motor 22. Again, although four walls 90 are shown, any number of walls, including a single wall, may be provided on the second side of the rotor 32.

Figure 44:
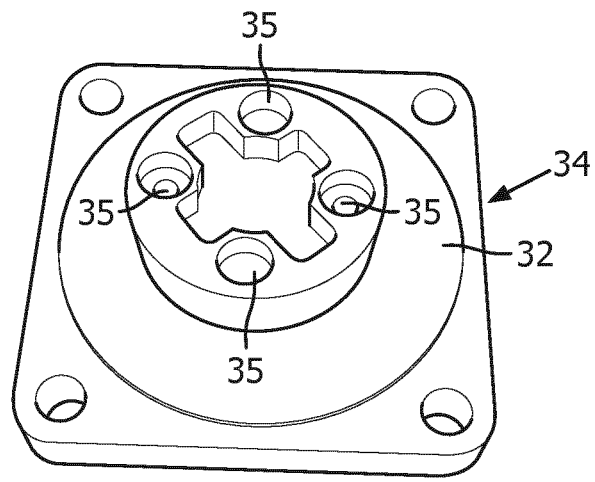
FIGS. 44-45 show examples of how the stator and rotor are mounted together when assembled in the rotary control valve on the first side.
Figure 45:
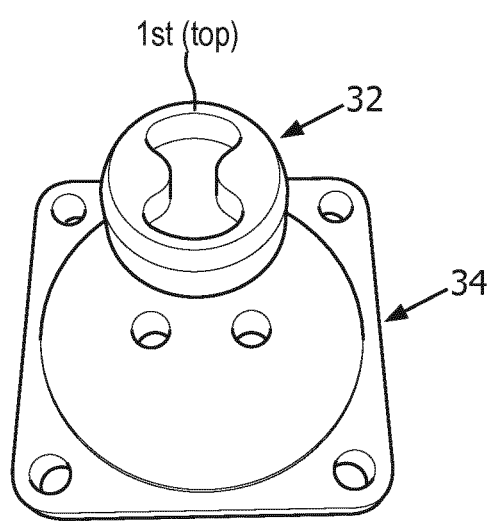

In another embodiment, such as shown in FIGS. 44 and 45, for example, the product rotor 32 does not include communicating ports and openings, but instead includes depressions for connection and fluid communication. FIG. 44 illustrates a second side of a product rotor 32 with an alternately shaped receiving portion 88B. Indents 35 are provided in the body of the rotor 32 for receipt of the biasing mechanisms 36 (provided between the rotor and driver 30). On the first side of this product rotor 50, as shown in FIG. 45, there is provided a symmetrical depression 94A. The symmetrical depression 94A is configured to open or close communication between the sieve beds 102, 104 as it rotates between steps in a PSA process. The design of the depression 94A allows for communication between the beds even as the rotor rotates between two steps of the process. In other words, there can be a change of state of the "valves" on the air side, and no change of state of the "valves" on the oxygen side, due to this feature.

The number, size and/or dimensions of the above described cavities, depressions, and ports vary depending upon the selected step process being employed by the module assembly 100.

As previously mentioned, the motor 22 is programmable to implement different PSA balance processes or cycles to rotate the shaft 24 (and thus the rotors 32, 48) through a 360 degree cycle to feed, balance, purge, etc. gases between the sieve beds 102, 104 and product storage tank 106, for example. The PSA cycles controllable and employed by the rotary control valve 10 and module assembly 100 disclosed herein include those with one, two, or three step feed phase and a zero, one, or two step equalization phase. As noted herein, an oxygen side balance process, or OSB process, is a PSA process step where the pressure balance occurs by opening valves on the product (O2) side of the sieve beds. In addition, the compressed air is fed to one sieve bed at a time, never both, and the exhaust ports of each bed are closed during the balance steps to assist with the balancing. In a true OSB process, there are no overlapping feed valves and the exhaust valves are closed during balance steps. However, it is understood by one of ordinary skill in the art that very slight overlap may occur in some cases, e.g., to smooth out any load on the compressor.

In each PSA balance cycle, the stepping motor 22 is programmed to find a home position (or zero position), and then progress through two or more steps in a 360 degree cycle. A step includes rotating the rotors 32, 48 (via rotation shaft 24) from one position to another position, stopping, and dwelling for a period of time. Accordingly, the locations for stopping rotation about the 360 degree cycle may be determined based on the division of the full cycle by the desired number of steps (e.g., 360/#steps). In accordance with embodiments as disclosed herein, the disclosed rotary control valve 10 may employ in 2-, 4-, 6-, 8-, and 10-step gas separation processes, for example. As such, a two-step process includes steps every 180 degrees. A four step process would include steps/stops every 90 degrees. A six step process would include stops every 60 degrees. An eight step process would include steps every 45 degrees. A ten step process would include stops every 36 degrees.

The dwelling time at each step may be determined based on testing and experimentation.

Several exemplary methods of employing a selected balance process using the disclosed rotary valve 10 and module assembly 100 in an oxygen concentrator are described in greater detail below. One of ordinary skill in the art shall understand the processes, implementation, and effects associated with each step noted below, including feeding, equalizing, balancing, and purging the sieve beds. Accordingly, features associated with each step for each noted balance process, are not necessarily described in great detail. Generally, however, it is noted that the act of feeding a bed includes delivering air to a bed using an air side 14 of the valve 10. In some cases, feeding may include feeding air and purified oxygen gas to a sieve bed. Exhausting a bed includes withdrawing any gases from the bed. In some cases, the bed pressure may be higher than atmospheric pressure, and thus opening a valve, e.g., to expel through muffler, will allow exhaust flow out of the bed. In other cases, the exhaust may be via force, e.g., through suction, and muffler 82.

Balancing the beds, also referred to as equalizing the beds, refers to balancing or equalizing gas flow—and thus the pressure—between the beds. Reference to pre-balancing (Bal(Pre)) and post-balancing (Bal(Post)) refers to first and second parts of balancing steps, respectively. That is, a first part of balancing (Bal(Pre)) is before a point of equal pressure balance (e.g., both being fed), whereas the second part of balancing is after the point of pressure balance. The connection of the beds during balancing or equalizing is on the oxygen side (product side, or top side), of the beds. Purging refers to connecting the beds together such that one bed (e.g., bed A) delivers gas to the other bed (e.g., bed B). Thus, purging bed B refers to bed B having a pressure increase because of (purge) gas received from bed A. Purging may be induced by the application of pressurized air or gas into one of the beds.

In one embodiment, a two-step PSA process, without a pressure equalization step, is implemented by the assembly 100 using the rotary control valve 10. The rotors of the rotary control valve are rotated by rotating the shaft 180 degrees twice. The position of the shaft, and thus the position of the rotors, controls the feed to each sieve bed. For example, in an embodiment, at a shaft angle of zero degrees (or its home position, or 360 degrees), Bed A is fed while Bed B is exhausted. At a shaft angle of 180 degrees Bed B is fed while Bed A is exhausted.

Figures 23, 24:
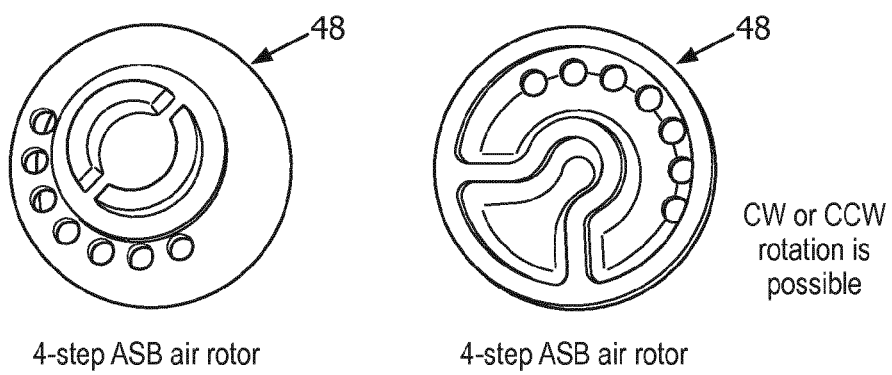
FIGS. 23 and 24 show a first side and a second side, respectively, of an exemplary rotor for use in the rotary control valve on its second side during the 4-step process of FIG. 22, in accordance with an embodiment.

In a first illustrated exemplary configuration of an oxygen concentrator, schematically shown in FIG. 22, a four (4)-step PSA air side balance process is implemented, by using the assembly 100, the rotary control valve 10 and other system components, including the compressor 80 and the muffler 82, which are schematically illustrated. FIGS. 23 and 24 show a first side and a second side, respectively, of an exemplary rotor 48 for use in the rotary control valve 10 on its air side 14 during the 4-step PSA air side balance process. The first side (FIG. 23) of the rotor 48 faces the driver 46, which is rotatably connected to the shaft 24 of the stepping motor 22. The angle of the rotor (i.e., the rotation angle of the shaft which rotates the rotor to each step) controls the percentage of air side balance. With this rotor 48, the rotary control valve 10 provides functionality that is equivalent to two 3-way valves. In this 4-step PSA air side balance process, only the air side is balanced in each step, and there is no oxygen side balance function. Valve 156 schematically represents the product feed (O2) into the product tank from the bed(s) via the product side 12 of the valve 10. One-way valves 138 are also schematically shown in FIG. 22.

More specifically, FIG. 25 is a chart illustrating examples of the feeds and exhausts of the Beds A and B at each of the steps of the 4-Step PSA air side balance process. In Step 1, wherein the angle of the shaft 24 is zero (0), i.e., in a home position, Bed A receives feed while Bed B is exhausted. The step time at Step 1 is approximately 5.00 seconds. In Step 2, at a shaft angle of 90 degrees, Beds A and B both receive feed for a time of approximately 0.80 seconds, and thus the beds are balanced. In Step 3, at a shaft angle of 180 degrees, Bed B is fed while Bed A is exhausted for a time of approximately 5.00 seconds. In Step 4, with the shaft rotated to 270 degrees in the cycle, Beds B and A are both fed, and thus balanced, for a time of approximately 0.80 seconds.

Based on the exemplary step times noted above for each step, the total cycle time of the rotary valve (to rotate 360 degrees) is approximately 11.60 seconds.

In a second exemplary configuration of an oxygen concentrator, schematically shown in FIG. 26, a 4-step PSA double side balance (DSB) (i.e., air and oxygen side) process is implemented, using the assembly 100, the rotary control valve 10, and other system components, including the compressor 80 and the muffler 82. FIGS. 27 and 28 show a first side and a second side, respectively, of an exemplary rotor 48 for use in the rotary control valve 10 on its air side 14 during this 4-step double side balance process. The first side (FIG. 27) of the air side rotor 48 faces the driver 46 on the air side, which is rotatably connected to the shaft 24 of the stepping motor 22.

FIGS. 29 and 30 show a first side and a second side, respectively, for an exemplary rotor 32 for use in the rotary control valve 10 on its oxygen side 12. The second side (FIG. 30) of the oxygen side rotor 32 faces the driver 30 which is rotatably connected to the shaft 24 of the stepping motor 26 on the oxygen side. With these rotors 32 and 48 therein, the rotary control valve 10 provides functionality that is equivalent to two 3-way valves and one 3-way valve. In this 4-step PSA DSB process, in addition to balancing the air side in each step, a two-valve function is added to the oxygen side, with both being balanced at each step (single step to balance the beds). The disclosed rotary control valve enables the air side percentage to be reduced or adjusted in to accommodate the double side balance (whereas prior art systems normally have an air side that dominates the balance step). Valve 156 schematically represents the product feed (O2) into the product tank from the bed(s) via the product side 12 of the valve 10. One-way valves 138 are also schematically shown in FIG. 26.

Figures 31, 32:
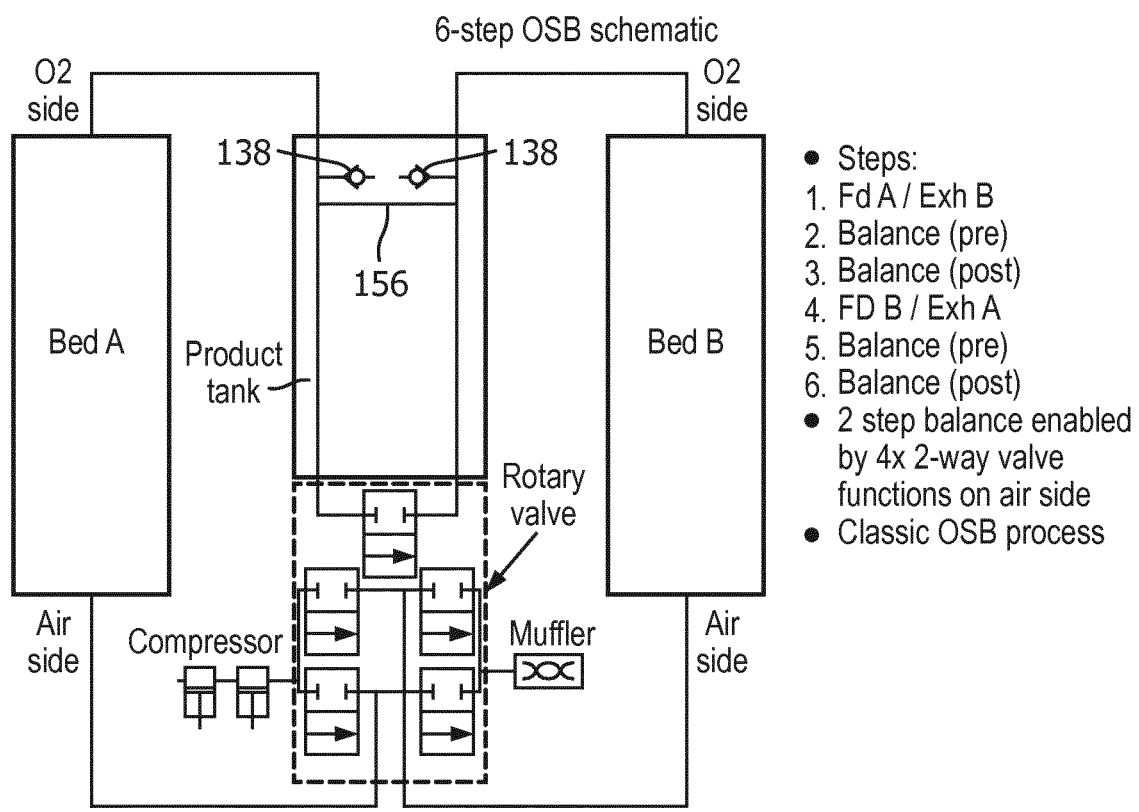
FIG. 31 is a chart illustrating the feeds, exhausts, and balancing of beds in the assembly at each of the steps of the 4-step process of FIG. 26.
FIG. 32 illustrates a schematic diagram of valves replaced by the disclosed rotary control valve for a 6-step oxygen side PSA process in the disclosed assembly, in accordance with an embodiment.

More specifically, FIG. 31 is a chart illustrating examples of the feeds, exhausts, and balancing of the Beds A and B in the assembly 100 at each of the steps of the 4 Step PSA double side balance process. In Step 1, for a time of approximately 5.00 seconds, the angle of the shaft 24 is zero (0), i.e., in a home position, and Bed A receives feed while Bed B is exhausted. In Step 2, at a shaft angle of 90 degrees, Beds A and B both receive feed and are balanced for a time of approximately 0.80 seconds. In Step 3, at a shaft angle of 180 degrees, Bed B is fed while Bed A is exhausted for a time of approximately 5.00 seconds. In Step 4, with the shaft rotated to 270 degrees in the cycle, Beds B and A both receive feed and are balanced for a time of approximately 0.80 seconds.

Based on the exemplary step times noted above for each step, the total cycle time of the rotary valve (to rotate 360 degrees) is approximately 11.60 seconds.

In a third exemplary configuration, schematically shown in FIG. 32, a six (6)-step PSA oxygen side balance (OSB) process is implemented. FIGS. 33 and 34 show a first side and a second side, respectively, of an exemplary rotor 48 for use in the rotary control valve 10 on its air side 14 during this 6-step OSB process. The first side (FIG. 33) of the air side rotor 48 faces the driver 46 which is rotatably connected to the shaft 24 of the stepping motor 22. FIGS. 35 and 36 show a first side and a second side, respectively, for an exemplary rotor 32 for use in the rotary control valve 10 on its oxygen side 12. The second side (FIG. 36) of the oxygen side rotor 32 faces the driver 30 which is rotatably connected to the shaft 24 of the stepping motor 22 on the oxygen side.

Figure 43:
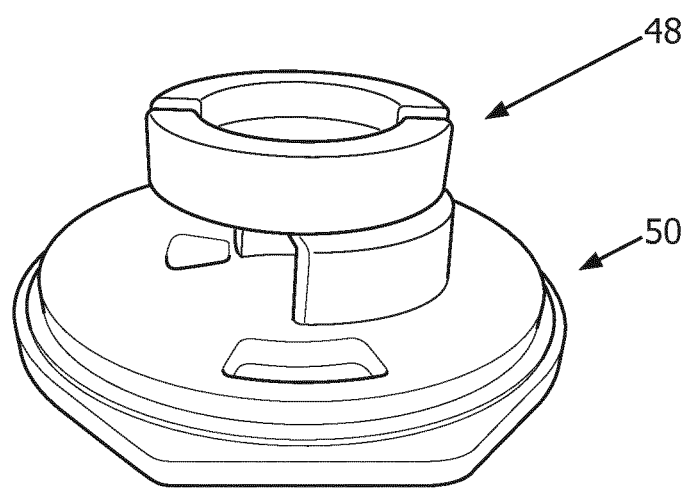

Alternatively, in another embodiment, rotors of a different design may be utilized. FIGS. 38 and 39 respectively show a first side of an exemplary stator 50 in the form of a plate and a second side of an exemplary rotor 48, for use in the rotary control valve 10 on its air side 14 during a 6-step OSB process. The first side of the air side rotor 48 (the top of the rotor 48 as shown in FIG. 39) faces the driver 46 on the air side. FIGS. 40 and 41 respectively show a first side of an exemplary stator 34 in the form of a plate and a first side of an exemplary rotor 32, for use on the oxygen side 12 of the rotary control valve 10. The first side (top side of the rotor 32 in FIG. 41, including the depression) of the oxygen side rotor 32 faces the respective driver 30. FIGS. 42-43 show examples of how the stator 50 and rotor 48 of the air side are mounted together, when assembled in the rotary control valve. FIGS. 44-45 show examples of how the stator 34 and rotor 32 of the product/oxygen side are mounted together, when assembled in the rotary control valve.

When either configuration of these rotors 32 and 48 is provided in the rotary control valve, the rotary control valve 10 provides functionality that is equivalent to four 2-way valves and one 2-way valve. In this 6-step process, two step balance is enabled by four times the 2-way valve functions on the air side. Valve 156 schematically represents the product feed (O2) into the product tank from the bed(s) via the product side 12 of the valve 10. One-way valves 138 are also schematically shown in FIG. 32.

FIG. 37 is a chart illustrating examples of the feeds, exhausts, and balancing of the Beds A and B in the assembly 100 at each of the steps in the 6-step OSB process. For a time of approximately 5.00 seconds in Step 1, the angle of the shaft 24 is zero (0), i.e., in a home position, and Bed A receives feed while Bed B is exhausted. In Step 2, at a shaft angle of 60 degrees, Bed A continues to receive feed and the balancing process of the beds begins (e.g., half balanced, or pre-balanced) (e.g., such as by opening valve 156, at the top/oxygen side of the beds) for a time of approximately 0.40 seconds. In Step 3, at a shaft angle of 120 degrees, Bed B receives feed and the balancing process continues for a time of approximately 0.40 seconds. After this time, the beds are balanced (e.g., pressure is equalized via gas flow therebetween). In Step 4, at a shaft angle of 180 degrees, Bed B is fed while Bed A is exhausted for a time of approximately 5.00 seconds. In Step 5, at a shaft angle of 240 degrees, Bed B continues to receive feed and the beds are pre-balanced for a time of approximately 0.40 seconds. In Step 6, at a shaft angle of 300 degrees, Bed A receives feed and the beds are post-balanced for a time of approximately 0.40 seconds. After this time, the beds are again balanced.

Based on the exemplary step times noted above for each step, the total cycle time of the rotary valve (to rotate 360 degrees) is approximately 11.60 seconds.

Figure 37A:
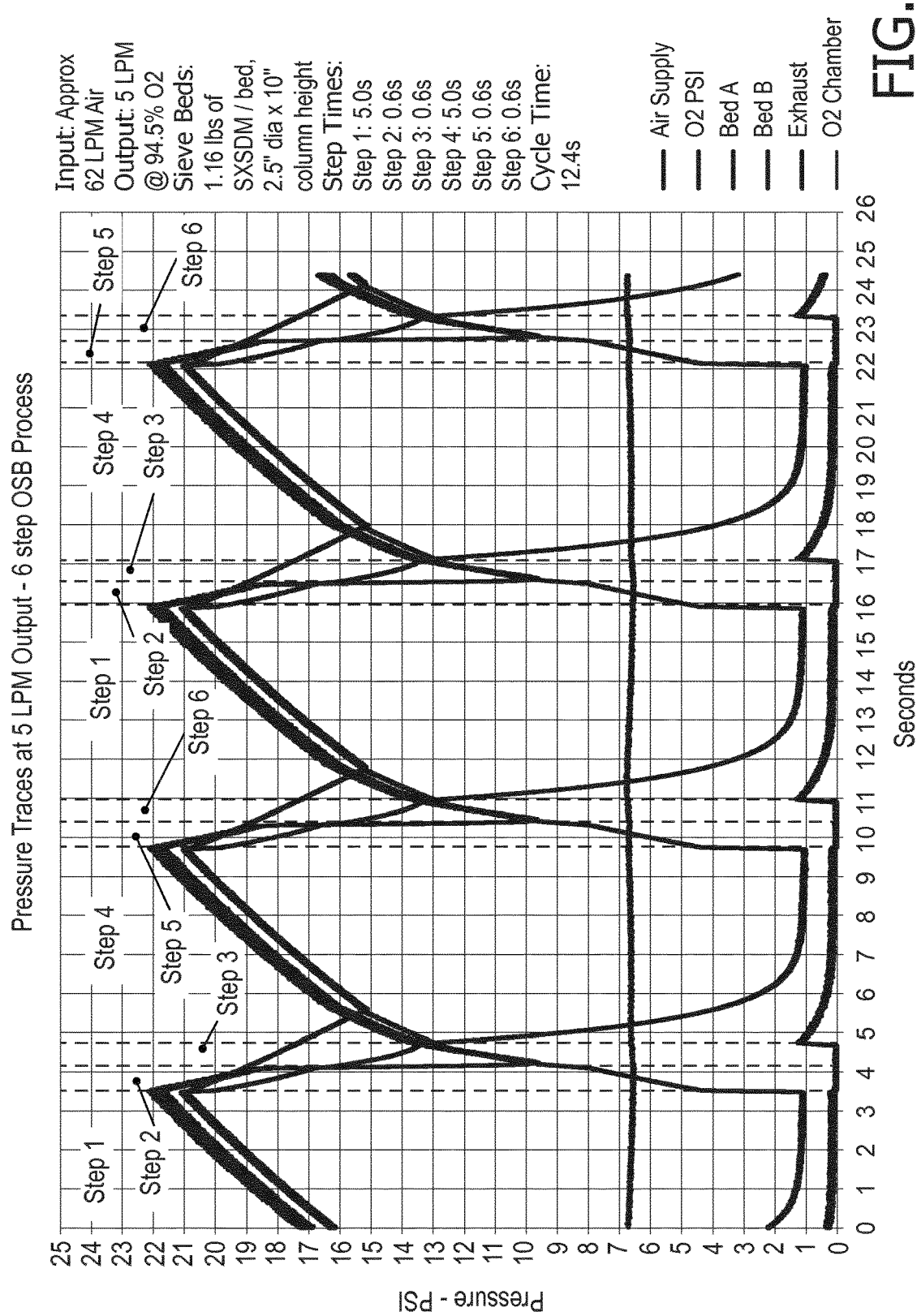
FIG. 37A is a pressure curve graph relating to the steps in the 6-step process of FIG. 37.

FIG. 37A is a pressure curve graph showing the pressures (PSI) at each second for air supply, O2 PSI, Bed A, Bed B, exhaust, and the O2 chamber and how they vary at each step during a repeated 6-step PSA cycle of FIG. 37. More specifically, this graph shows approximately 23.2 seconds of data, which equates to two complete cycles of this specific process.

Figure 46:
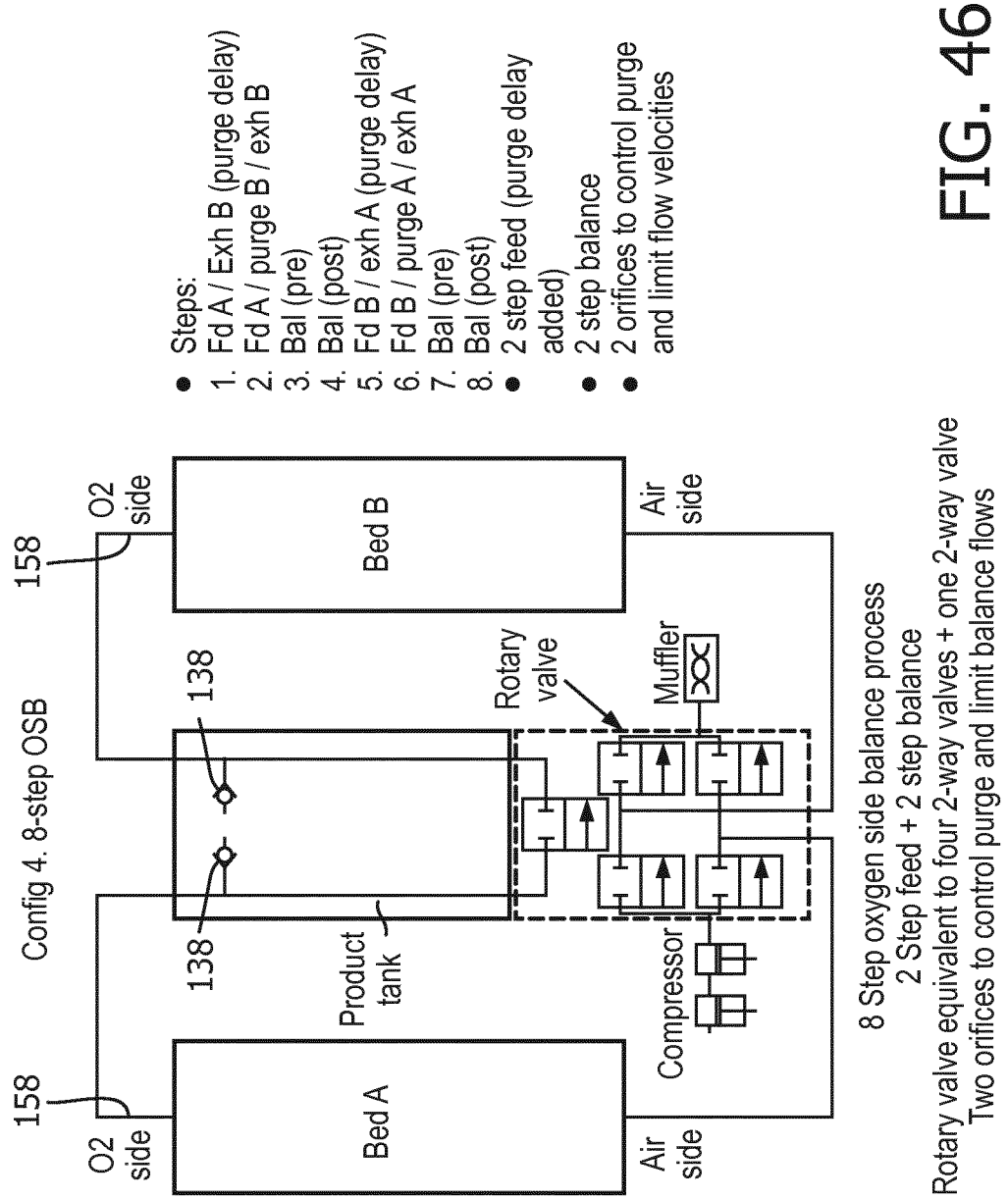
FIG. 46 illustrates a schematic diagram of valves replaced by the disclosed rotary control valve for an 8-step oxygen side PSA process in the disclosed assembly, in accordance with an embodiment.

In a fourth exemplary configuration, schematically shown in FIG. 46, an eight (8)-step PSA oxygen side balance (OSB) process is implemented.

FIGS. 47 and 48 show a first side and a second side, respectively, of an exemplary rotor 48 for use in the rotary control valve 10 on its air side 14 during the 8-step OSB process. The first side (FIG. 47) of the air side rotor 48 faces the driver 46 which is rotatably connected to the shaft 24 of the stepping motor 22. FIGS. 49 and 30 show a first side and a second side, respectively, for an exemplary rotor 32 for use in the rotary control valve 10 on its oxygen side 12. The second side (FIG. 50) of the oxygen side rotor 32 faces the driver 30 which is rotatably connected to the shaft 24 of the stepping motor 22 on the oxygen side. With these rotors 32 and 48, the rotary control valve 10 provides functionality that is equivalent to four 2-way valves and one 2-way valve. The 8-step OSB process includes 2 step feed (with purge delay added) and 2 step balance. Accordingly, two orifices 158 are provided adjacent to the oxygen sides of the beds A and B to control purge and limit flow velocities. Valves may optionally be provided in the orifices 158. One-way valves 138 to the product storage tank 106 are also schematically shown in FIG. 46.

Figure 52:
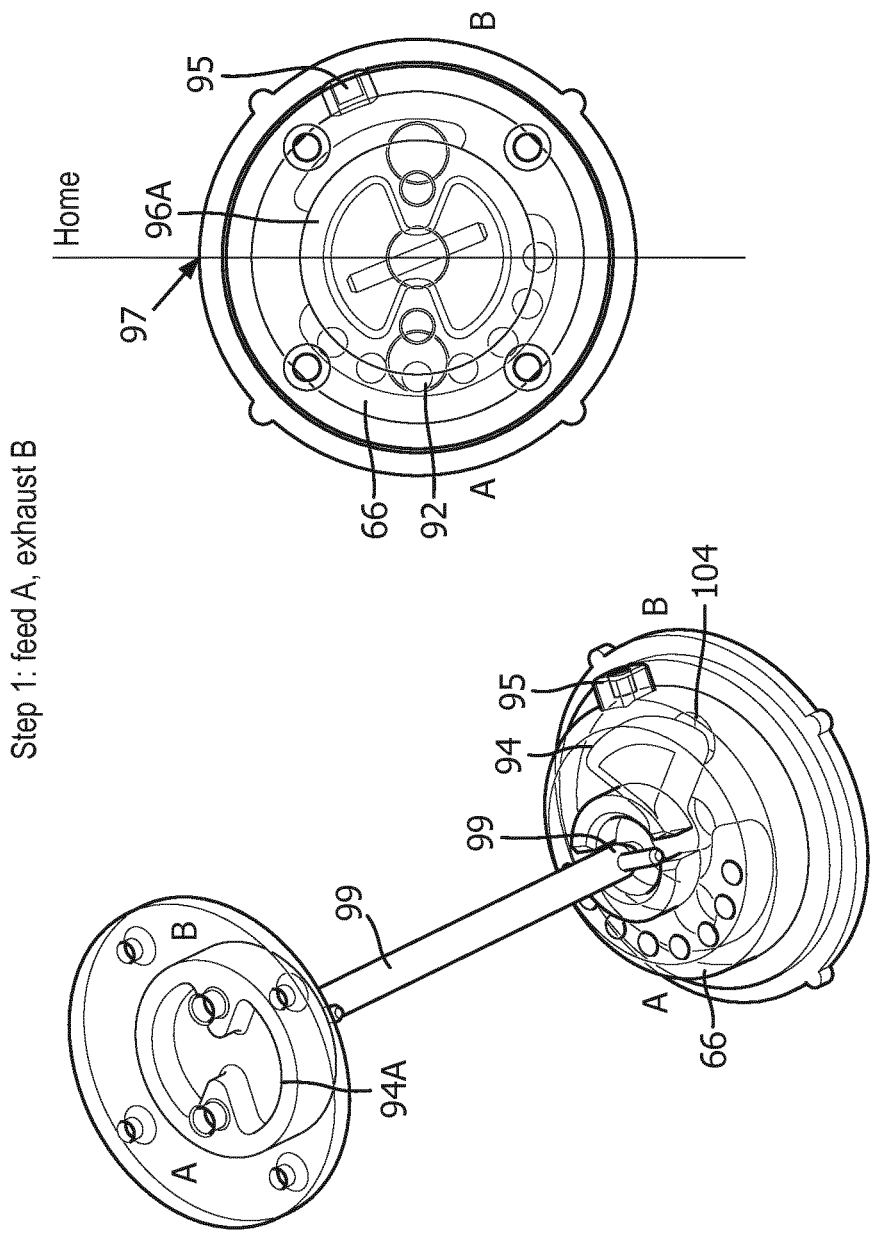
FIGS. 52-59 demonstratively illustrate rotation of the feed and exhaust rotors of the rotary control valve in each of the steps 1-8 of the 8-step process of FIG. 46.

FIG. 51 is a chart illustrating examples of the feeds, exhausts, and purging and balancing of the Beds A and B in the assembly 100 at each of the steps during the 8 step OSB process. FIGS. 52-59 demonstratively illustrate rotation of the rotors 32 and 48 in each of the steps 1-8 of FIG. 51, showing relative movement of the cavities, depressions, and/or ports of the rotors 32 and 48 to the ports of the stators 34 and 50, with the shaft 24 moving the rotors to each step position of the 8-step OSB process. FIG. 52 illustrates the rotors 32, 48 in a home position (1st position). In Step 1, the angle of the shaft 24 is zero (0), i.e., in this home position, and Bed A receives feed (e.g., orifice(s) 92 of rotor 48 are aligned with port 66 of stator 50) while Bed B is exhausted (e.g., bell shaped depression 94 of rotor limits communication with port 62 of air stator 50). The rotary control valve may dwell or stay in its position at Step 1 for a time of approximately 3.0 seconds.

Figure 53:
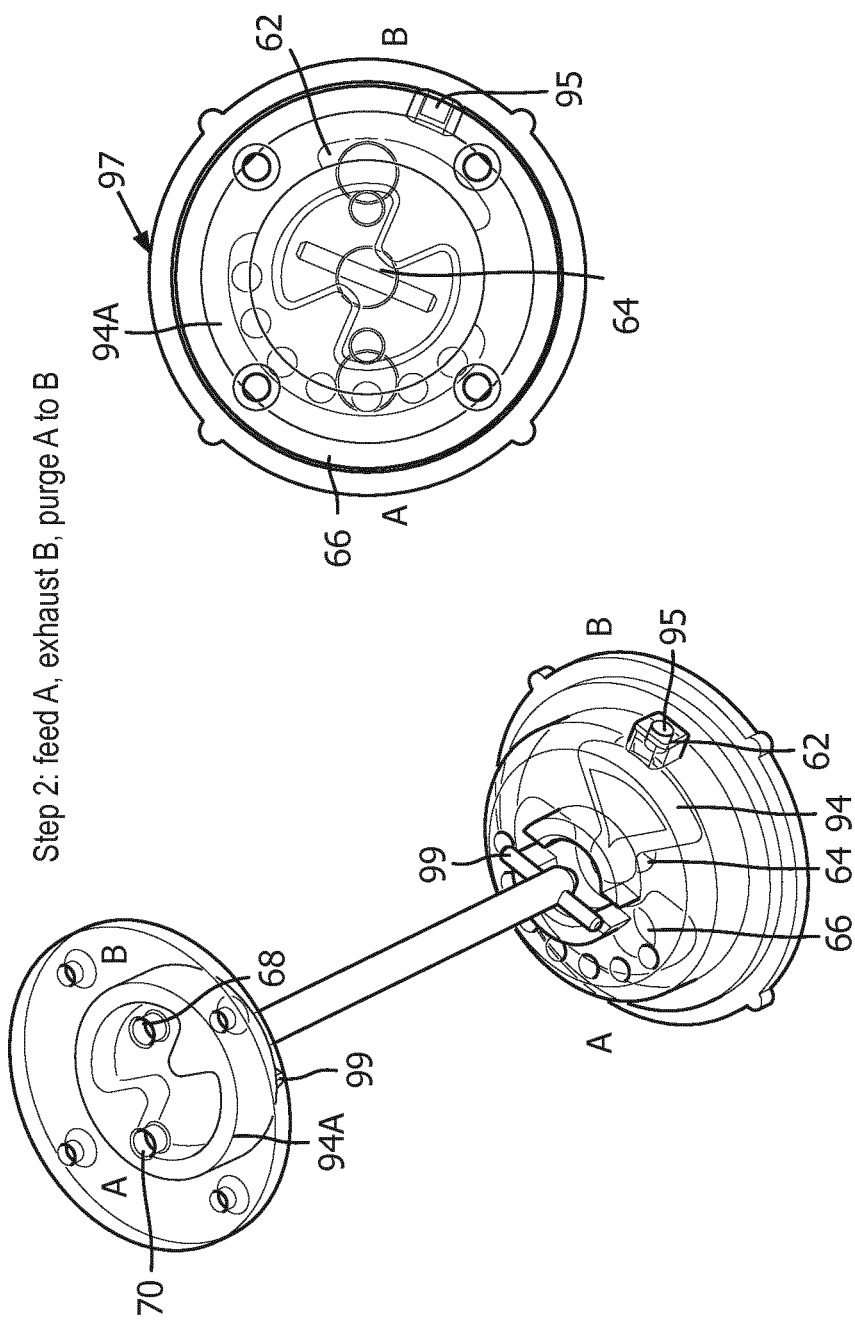

FIG. 53 illustrates the rotors in a second position. In Step 2, at a shaft angle of 45 degrees, Bed A continues to receive feed (orifice(s) 92 of rotor 48 are aligned with port 66 of stator 50), and Bed B continues to exhaust (part of bell shaped depression 94 still limits communication with port 62 of air stator 50) as well as purge (via receipt of gas from Bed A; e.g., bell shaped depression 94A of product rotor 32 moves in alignment with ports 68 and 70 of product stator 34 to fluidly connect the beds A and B), for a time of approximately 1.75 seconds.

Figure 54:
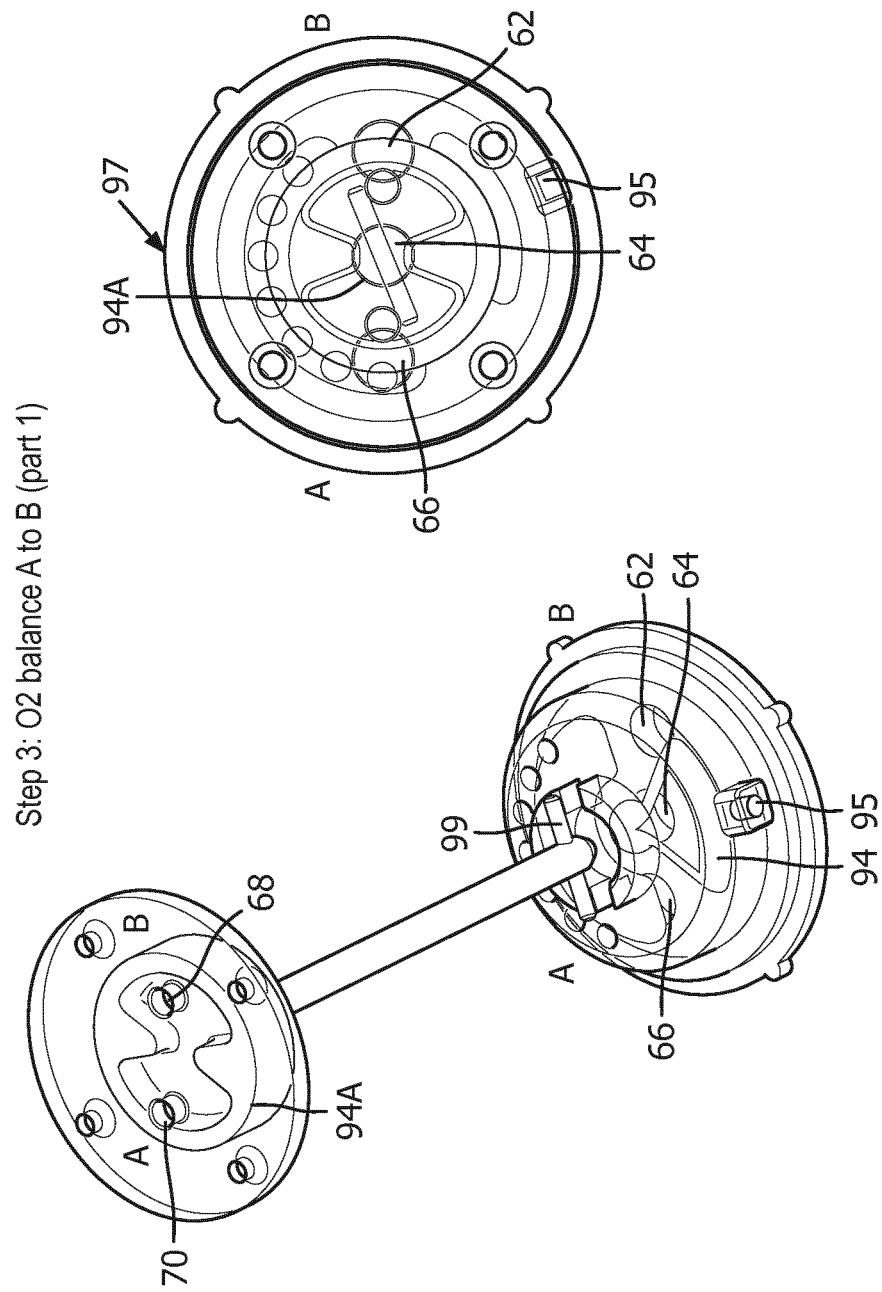

FIG. 54 illustrates the rotors in a third position. In Step 3, at a shaft angle of 90 degrees, Bed A receives feed and the beds are balanced (e.g., bell shaped depression 94A of product rotor 32 maintains communication with ports 68 and 70 of product stator 3). Also, bell shaped depression 94 of air rotor 48 moves away from alignment with any of the ports of air stator 50. The rotary control valve may dwell or stay in its position at Step 3 for a time of approximately 0.5 seconds.

Figure 55:
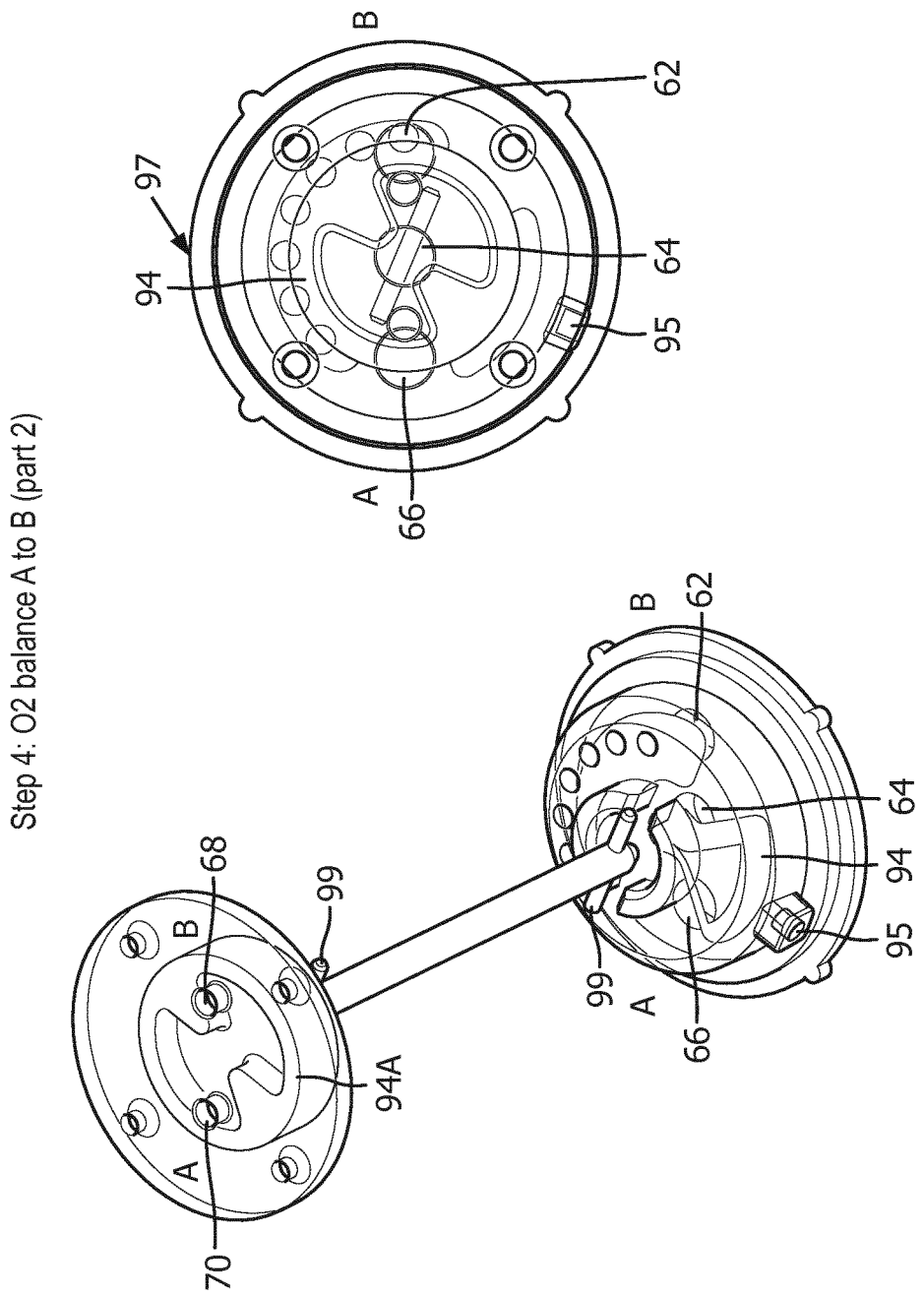

FIG. 55 illustrates the rotors in a fourth position. In Step 4, at a shaft angle of 135 degrees, Bed B is fed (e.g., orifice(s) 92 of rotor 48 are aligned with port 62 of stator 50) and the beds are balanced for a time of approximately 0.8 seconds.

Figure 56:
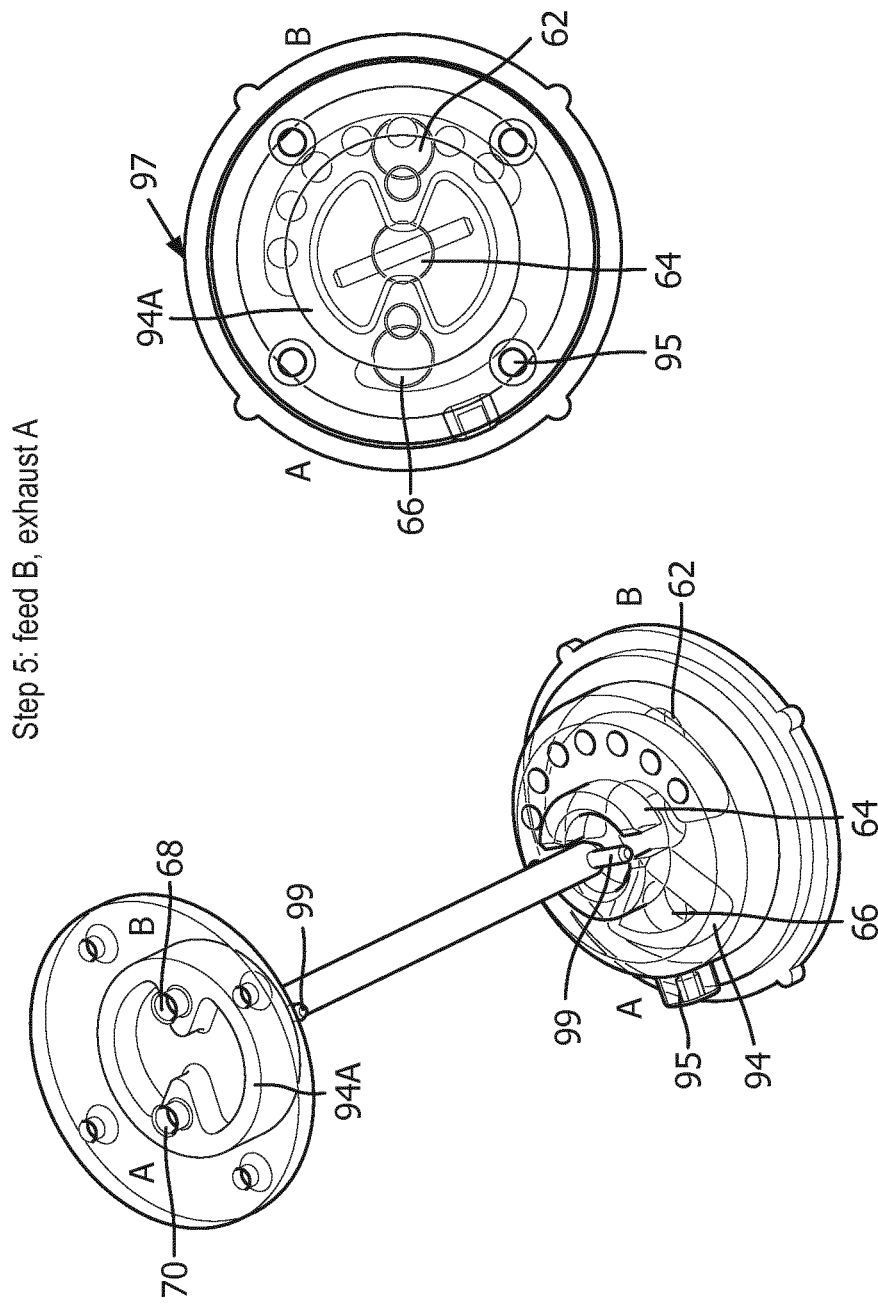
Figure 57:
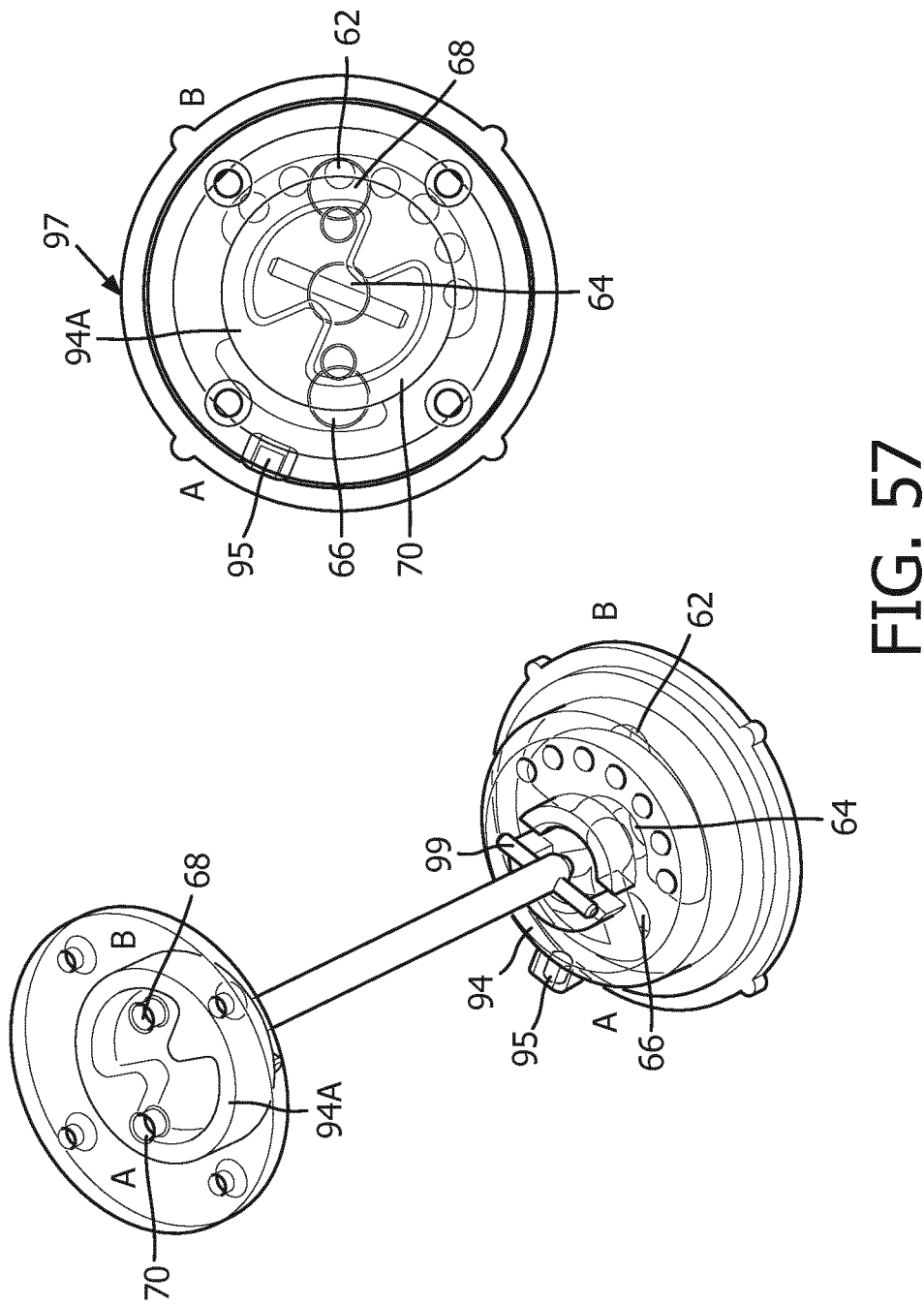

FIG. 56 illustrates the rotors in a fifth position. In Step 5, at a shaft angle of 180 degrees (from its home position), Bed B continues to receive feed (via alignment of orifice(s) 92 and port 62), while Bed A is exhausted (e.g., bell shaped depression 94 of air rotor 48 moves in alignment with ports 66) for a time of approximately 3.0 seconds. Also, bell shaped depression 94A of product rotor 32 moves away from alignment with any of the ports of product stator 34, thus stopping communication between the beds. FIG. 57 illustrates the rotors in a sixth position. In Step 6, at a shaft angle of 225 degrees, Bed B continues to receive feed, and Bed A continues to exhaust as well as purge (via receipt of gas from Bed B; e.g., bell shaped depression 94A of product rotor 32 moves in alignment with ports 68 and 70 of product stator 34 to fluidly connect the beds B and A). The rotary control valve may dwell or stay in its position at Step 6 for a time of approximately 1.75 seconds.

Figure 58:
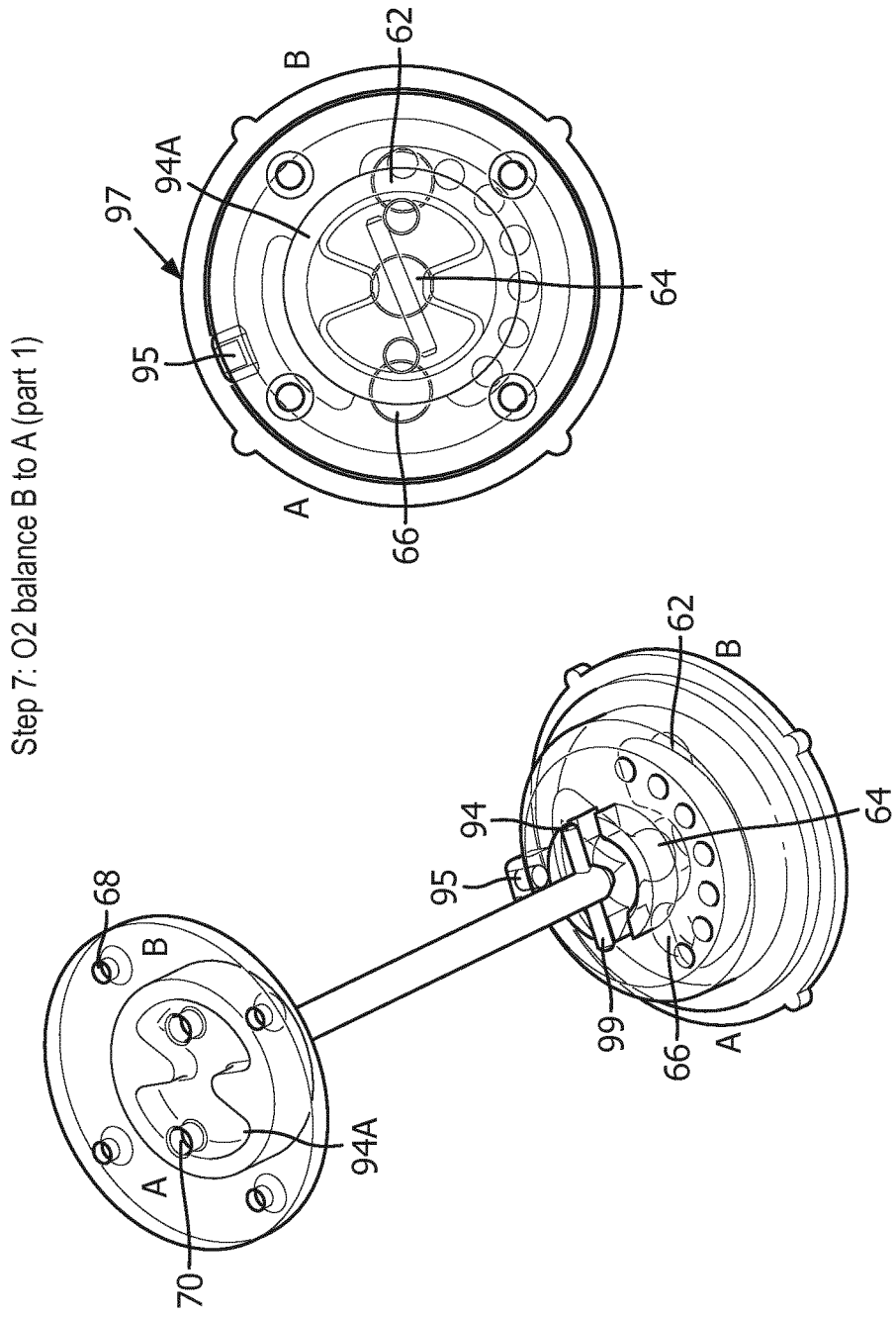
Figure 59:
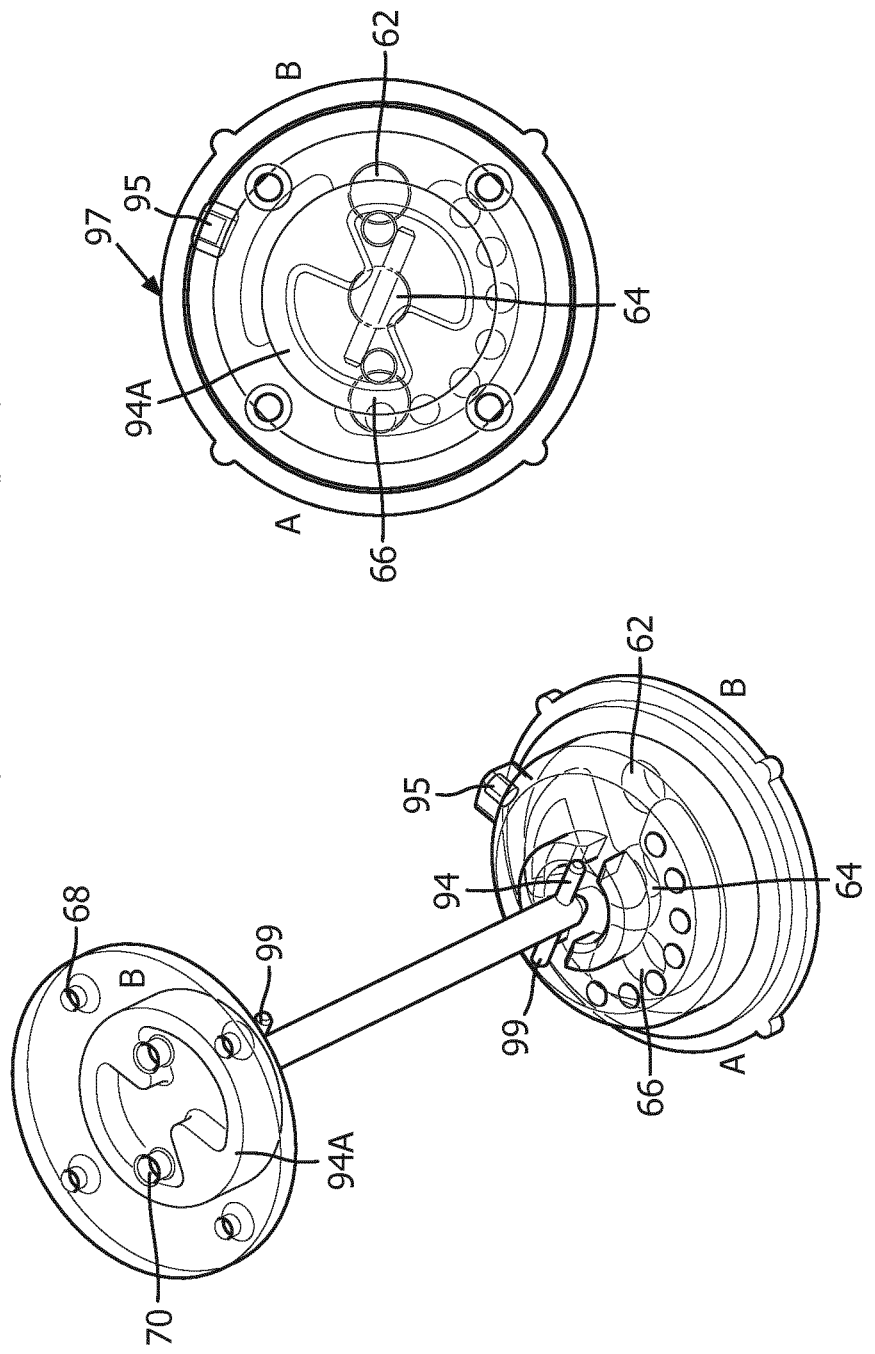

FIG. 58 illustrates the rotors in a seventh step. In Step 7, at a shaft angle of 270 degrees, Bed B receives feed (e.g., via orifice(s) 92 of air rotor 48 being aligned with port 66 of air stator 50) and the beds are balanced (via bell shaped depression 94A in rotor 32) for a time of approximately 0.5 seconds. FIG. 59 illustrates the rotors in an eighth position. In Step 8, at a shaft angle of 315 degrees, Bed A is fed (e.g., orifice(s) 92 of rotor 48 are aligned with port 66 of stator 50) and the beds are balanced for a time of approximately 0.8 seconds.

Based on the exemplary step times noted above for each step, the total cycle time of the rotary valve (to rotate 360 degrees) is approximately 12.10 seconds.

Also shown in the illustrative embodiment of FIGS. 52-59 are utilization of a cylindrically-shaped magnet 95 and a Hall-effect sensor 97. The illustrated magnet 95 and sensor 97 of FIGS. 52-59 may be similarly utilized in other embodiments and processes described herein and are not limited to use in an 8-step process or with the illustrated rotors of FIGS. 52-59. The magnet 95 is sensed by the Hall Effect sensor 97 to signal (e.g., to the controller) that the home position has been found. This may be used during the start-up routine, for example, to establish an absolute rotational location for the motor shaft. The subsequent process steps (shaft rotation locations) are located a certain number of degrees from the home position. The magnet 95 and sensor 97 have specifications to suit this purpose. Pins 99 are provided to connect the rotating shaft to a rotating driver (not shown here for explanatory purposes only; e.g., see drivers 30 and 46).

Figure 60:
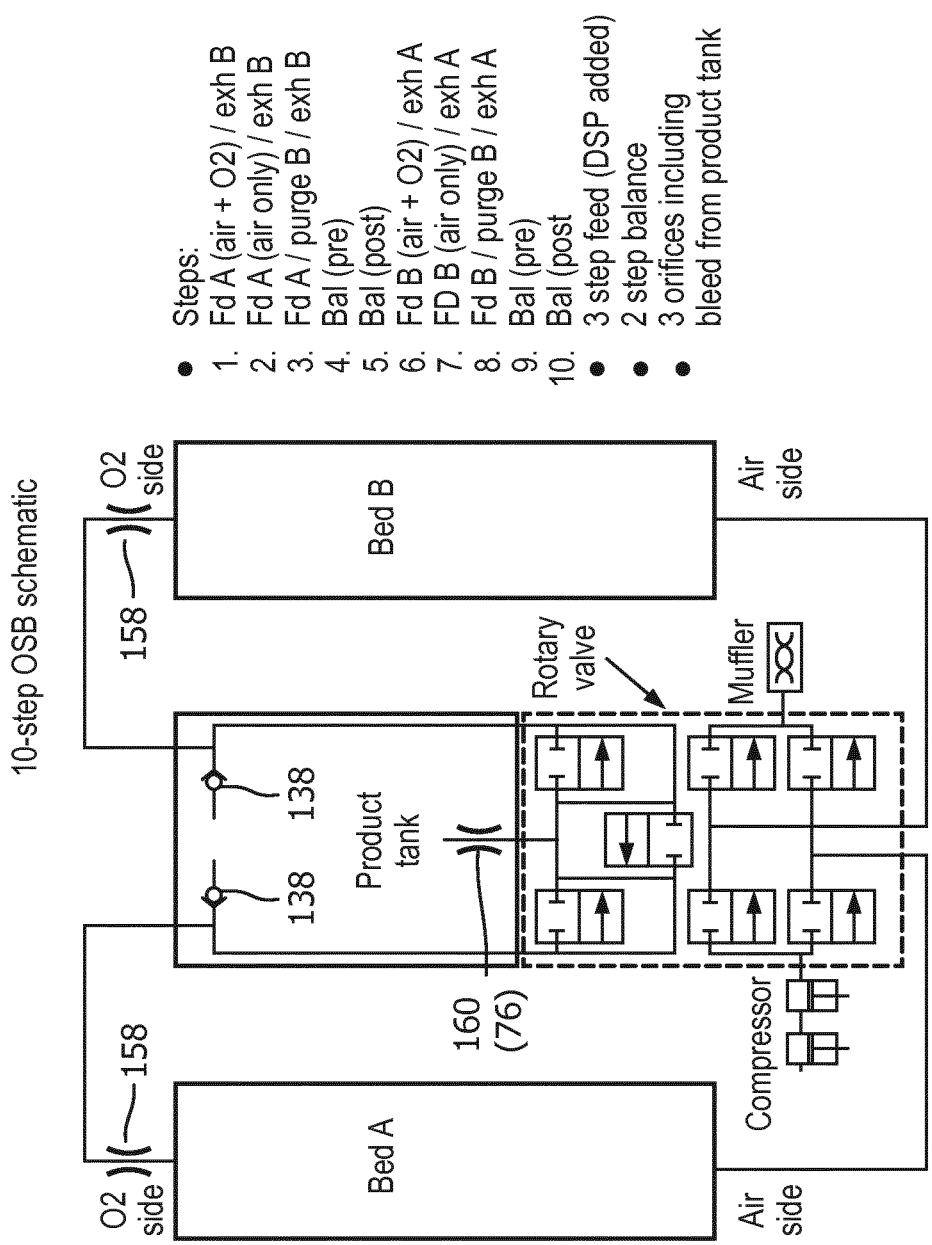
FIG. 60 illustrates a schematic diagram of valves replaced by the disclosed rotary control valve for a 10-step oxygen side PSA process in the disclosed assembly, in accordance with an embodiment.

In a fifth exemplary configuration, schematically shown in FIG. 60, a ten (10)-step PSA oxygen side balance (OSB) process is implemented by the assembly 100. FIGS. 62 and 63 respectively show a first side of an exemplary stator 50 in the form of a plate and a second side of an exemplary rotor 48, for use in the rotary control valve 10 on its air side 14 during a 10-step OSB process. The second side (FIG. 63) of the air side rotor 48 faces the stator 50 on the air side. FIGS. 64 and 65 respectively show a first side an exemplary stator 34 in the form of a plate and a first side of an exemplary rotor 32, for use in the rotary control valve 10 on its oxygen side 12. The first side (top side of the rotor 32 in FIG. 65) of the oxygen side rotor faces the stator 34.

When either configuration of these rotors 32 and 48 is provided in the rotary control valve, the rotary control valve 10 provides functionality that is equivalent to four 2-way valves and three 2-way valves. In this process, two-step balance is enabled as well as 3-step feed (double side feed (DSF) added) per ½ PSA cycle, totaling 10-steps per complete cycle. The balance steps use some product storage tank gas, as does one of the feed steps. Accordingly, in addition to two orifices 158 being provided adjacent to the oxygen sides of the beds A and B to control purge and limit flow velocities, a third orifice 160 is schematically provided between the rotary valve 10 and product storage tank 106, for bleeding from the tank 106. The third orifice 160 may represent, for example, the previously described orifice 76 as shown in FIG. 4. Valves may optionally be provided in the orifices 158, 160. One-way valves 138 to the product storage tank 106 are also schematically shown in FIG. 46.

FIG. 61 is a chart illustrating examples of the feeds, exhausts, purging, and balancing of the Beds A and B in the assembly 100 based on the movement of valves at each of the steps during the 10-step OSB process. In Step 1, the angle of the shaft 24 is zero (0), i.e., in a home position, and Bed A receives feed while Bed B is exhausted. Bed A is also purged in Step 1. The rotary control valve may dwell or stay in its position at Step 1 for a time of approximately one second. In Step 2, at a shaft angle of 36 degrees, Bed A continues to receive feed, and Bed B continues to exhaust. The rotary control valve may dwell or stay in its position at Step 2 for a time of approximately two seconds. In Step 3, at a shaft angle of 72 degrees, Bed A receives feed, Bed B exhausts, and Bed B is purged of N2 using O2 from the product tank and Bed A. The rotary control valve may dwell or stay in its position at Step 3 for approximately 2.0 seconds.

In Step 4, at a shaft angle of 108 degrees, Bed A is fed and the beds are pre-balanced, for a time of approximately 0.40 seconds. In Step 5, at a shaft angle of 144 degrees, Bed B receives feed, and the beds are post-balanced. The rotary control valve may dwell or stay in its position at Step 5 for a time of approximately 0.40 seconds. In Step 6, at a shaft angle of 180 degrees, Bed B continues to receive feed and is purged, while Bed A is exhausted. The rotary control valve may dwell or stay in its position at Step 6 for a time of approximately one second. In Step 7, at a shaft angle of 216 degrees, Bed B continues to receive feed, and Bed A continues to exhaust. The rotary control valve may dwell or stay in its position at Step 7 for a time of approximately two seconds. In Step 8, at a shaft angle of 252 degrees, Bed B is fed, Bed A is exhausted, and Bed A is purged of N2 using O2 from the product tank and Bed B. The rotary control valve may dwell or stay in its position at Step 8 for a time of approximately two seconds. In Step 9, at a shaft angle of 288 degrees, Bed B is fed and the beds are pre-balanced, for a time of approximately 0.40 seconds. In Step 10, at a shaft angle of 324 degrees, Bed A is fed and the beds are post-balanced, for a time of approximately 0.40 seconds.

Based on the exemplary step times noted above for each step, the total cycle time of the rotary valve (to rotate 360 degrees) is approximately 11.60 seconds.

As such, as understood by the described balance processes above, the disclosed rotary control valve 10 and module assembly 100 provides greater flexibility in changing the process for oxygen delivery. While known methods tend to implement one particular gas separation process, e.g., with the variables being the time spent at each process step, the disclosed valve 10 and assembly 100 allows for use of different variations of the rotor and stator components, and a reprogramming of the stepping motor (via a controller), to affect a different gas separation process control. Further, the rotary control valve 10 and/or module assembly 100 are easily scalable based on the system or environment it is employed in; for example, the valve 10 may be used in systems that are small, portable, and wearable, or system of larger scale, such as stationary or industrial size systems.

Because of the assembly and placement of parts in the disclosed rotary control valve 10—including the placement and incorporation of the motor 22 and shaft 24 between the symmetrically designed rotor/stator combinations at each end 12, 14 of the valve 10—a more compact configuration of the rotary control valve 10 is established that is still capable of implementing any number of step balance processes. As such, as demonstrated by the schematic drawings in FIGS. 22, 26, 32, 46, and 60, this one valve 10 replaces the functions of multiple solenoid valves (e.g., up to nine solenoid valves, four on the air side, five on the product side) that are conventionally used in known prior art devices to control these same processes. Further, it eliminates extra connections and controllers between parts of the assembly (e.g., each prior art valve requiring piping connections, power, switching control, and timing input), as well as previous compromises made when considering factors of product output, separation efficiency, process complexity, size and materials cost.

The inherent symmetry of the design of the rotary control valve 10 leads to symmetrical and equivalent flow rates for both halves of a PSA cycle. Asymmetrical flows of traditional solenoid valves can lead to less than optimum PSA performance, or require compensation via an offsetting control technique, which adds uncertainty and complexity. Also, because the rotary control valve 10 provides both air side and oxygen side valve functions via a single motor, single shaft solution, the air separation process steps of the air side and the oxygen side valves are inherently synchronized, thus overcoming response time and control timing complexity of prior art solenoid valves. Additionally, a lead or lag in opening or closing a port can be designed in, if desired. The valve design allows for the possibility of designing a positive or negative angular offset between the oxygen side and the air side. It also allows for the possibility of partially open and partially closed ports, if so desired.

Further, traditional considerations and comprises—including cost, size, and weight of additional valves—are substantially if not entirely eliminated based on the design of the disclosed rotary control valve 10. The functions of this valve 10 are easily changed and its inclusion of reprogrammable components allows for different step process implementations. The mechanical architecture is such that the cost, size, and weight of the control valve 10 is the same, independent of the chosen process. The end result is a configurable valve assembly that externally appears the same, and is considerable equal in manufacturing cost, weight, size, and power consumption, that is capable of employing and controlling simpler 4-step processes as well as more complex 6-, 8-, and 10-step processes.

The system and/or environment in which the rotary control valve 10 and module assembly 100 are used is not intended to be limited. For example, as previously noted the valve 10/could be applied to medical oxygen concentrators used for supplemental oxygen therapy. It could also be used in industrial oxygen concentrators for non-medical use. The rotary control valve 10 may also be employed in other industrial and/or medical applications where a simple, low cost, compact multi-port, multi-function valve designed to separate air and a product gas would be desirable.

Further, as generally noted herethroughout, a number of additional parts may be used with the module assembly 100 in an oxygen concentrator, although they may not have been illustrated or described in detail herein. One of ordinary skill in the art recognizes that sensors and other mechanisms may be used with the valve 10 and assembly. For example, a transducer may be connected to the compressor 80 to assist in steps of the different balance processes. In one example, the transducer is used to measure a certain amount (e.g., 1 psi) of purge gas used to purge the bed(s).

Also, the materials used to form the parts of the rotary valve 10 and/or parts of the module assembly 100 are not intended to be limiting. In accordance with an embodiment, the housings 20, 21 and any number of its parts may be made of molded plastic. While materials such as plastics (e.g., Teflon) may be used to form or mold the rotors 32, 48, the plates of the stators 34, 50 may be formed from anodized aluminum (and machined to include ports therein). Seals may be formed from rubber, for example.

While the principles of the disclosure have been made clear in the illustrative embodiments set forth above, it will be apparent to those skilled in the art that various modifications may be made to the structure, arrangement, proportion, elements, materials, and components used in the practice of the disclosure.

It will thus be seen that the features of this disclosure have been fully and effectively accomplished. It will be realized, however, that the foregoing preferred specific embodiments have been shown and described for the purpose of illustrating the functional and structural principles of this disclosure and are subject to change without departure from such principles. Therefore, this disclosure includes all modifications encompassed within the spirit and scope of the following claims.

What is claimed is:

1. A rotary control valve comprising:
   a product end comprising a product housing containing a product rotor and a product stator therein, the product housing comprising a chamber therein for receipt of the product rotor and the product stator, the product rotor comprising a plurality of cavities configured for alignment with ports in the product stator;
   an air end comprising an air housing containing an air rotor and an air stator therein, the air housing comprising a chamber therein for receipt of the air rotor and the air stator, the air rotor comprising a plurality of cavities configured for alignment with ports in the air stator;
   a shaft operatively connected to the product rotor and the air rotor; and
   a motor configured to drive the shaft, wherein the motor is provided between the stators,
   wherein both of the chambers are configured to hold pressurized gas therein;
   wherein the product stator and the air stator enclose their respective rotors within the chambers of the housings; and
   wherein driving of the shaft is configured to rotate the product rotor and air rotor relative to their respective stators such that the cavities in each of the rotors selectively align with ports in their respective stators.

2. The valve according to claim 1, wherein rotors are configured to be rotated to different positions relative to their respective stators by the shaft and the alignment of the cavities of the rotors with the ports in the stators is determined based on a step in a selected PSA balance process, wherein each position is associated with one step in the selected PSA balance process.

3. The valve according to claim 1, further comprising a driver at each of the product end and the air end, the drivers being mounted to the shaft, each driver being operatively connected to the respective rotors within the product end and air ends and configured to rotate the respective rotors during driving of the shaft.

4. The valve according to claim 3, wherein each rotor has a mating surface corresponding to connective mating surface of its driver.

5. The valve according to claim 1, wherein the motor is a programmable stepping motor configured to drive the shaft through a plurality of steps throughout a 360 degree cycle, wherein the product rotor and air rotor are configured to be rotated to different positions relative to their respective stators about the 360 degree cycle.

6. A method for controlling a pressure swing adsorption (PSA) process using a rotary control valve, the rotary control valve comprising a product end and an air end, the product end comprising a product housing containing a product rotor and a product stator therein and an air end comprising an air housing containing an air rotor and an air stator therein, the product housing comprising a chamber therein for receipt of the product rotor and the air housing comprising a chamber therein for receipt of the air rotor, the product rotor comprising a plurality of cavities configured for alignment with ports in the product stator and the air rotor comprising a plurality of cavities configured for alignment with ports in the air stator, the rotary control valve further comprising a shaft operatively connected to the product rotor and the air rotor a motor configured to drive the shaft, a driver at each of the product end and the air end, the drivers being mounted to the shaft, each driver being operatively connected to the respective rotors within the product end and air end and configured to rotate the respective rotors during driving of the shaft, and biasing mechanisms provided between the drivers and the product and air rotors for biasing and sealingly engaging the product and air rotors towards their respective stators; wherein the method comprises:
   operating the motor;
   driving the shaft using the motor; and
   rotating the product rotor and the air rotor relative to their respective stators as a result of the driving of the shaft,
   wherein both of the chambers are configured to hold pressurized gas therein during use of the rotary control valve;

wherein the product stator and the air stator enclose their respective rotors within the chambers of the housings; and wherein the rotating of the product rotor and air rotor selectively aligns cavities in the rotors with ports of their respective stators.

7. The method according to claim 6, wherein the motor is a programmable stepping motor configured to drive the shaft through a plurality of steps throughout a 360 degree cycle, wherein the product rotor and air rotor are configured to be rotated to different positions relative to their respective stators about the 360 degree cycle, and wherein the method further comprises:

driving the shaft through the plurality of steps throughout the 360 degree cycle; and rotating the product rotor and the air rotor to different positions relative to their respective stators about the 360 degree cycle.

8. A rotary control valve comprising:

a product end comprising a product housing containing a product rotor and a product stator therein, the product housing comprising a chamber therein for receipt of the product rotor and the product stator, the product rotor comprising a plurality of cavities configured for alignment with ports in the product stator;

an air end comprising an air housing containing an air rotor and an air stator therein, the air housing comprising a chamber therein for receipt of the air rotor and the air stator, the air rotor comprising a plurality of cavities configured for alignment with ports in the air stator;

a shaft operatively connected to the product rotor and the air rotor; and a motor configured to drive the shaft;

a driver at each of the product end and the air end, the drivers being mounted to the shaft, each driver being operatively connected to the respective rotors within the product end and air end and configured to rotate the respective rotors during driving of the shaft; and biasing mechanisms provided between the drivers and the product and air rotors for biasing and sealingly engaging the product and air rotors towards their respective stators, wherein both of the chambers are configured to hold pressurized gas therein;

wherein the product stator and the air stator enclose their respective rotors within the chambers of the housings; and wherein driving of the shaft is configured to rotate the product rotor and air rotor relative to their respective stators such that the cavities in each of the product and air rotors selectively align with ports in their respective stators.

9. The valve according to claim 8, wherein rotors are configured to be rotated to different positions relative to their respective stators by the shaft and the alignment of the cavities of the rotors with the ports in the stators is determined based on a step in a selected PSA balance process, wherein each position is associated with one step in the selected PSA balance process.

10. The valve according to claim 8, wherein the motor is provided between the stators.

11. The valve according to claim 8, wherein each rotor has a mating surface corresponding to connective mating surface of its driver.

12. The valve according to claim 8, wherein the motor is a programmable stepping motor configured to drive the shaft through a plurality of steps throughout a 360 degree cycle, wherein the product rotor and air rotor are configured to be rotated to different positions relative to their respective stators about the 360 degree cycle.

13. A module assembly comprising:

a rotary control valve according to claim 8, and a sieve bed module configured to receive air from the rotary control valve and to output product gas.

14. The module assembly according to claim 13, wherein the sieve bed module comprises two molecular sieve beds.

15. The module assembly according to claim 13, further comprising a product storage tank for holding the product gas produced by the sieve bed module.

16. The module assembly according to claim 13, wherein the rotary control valve is positioned relatively below or under the product storage tank.

17. The valve according to claim 1, wherein the shaft extends through the motor and beyond ends of the motor in two directions.

18. The valve according to claim 1, further comprising support posts extending between and attached to the product and air housings to secure the housings together with the motor therebetween to form as assembly.

19. The valve according to claim 1, further comprising a first seal bearing provided around a first end of the shaft and within the product housing and a second seal bearing provided around a second end of the shaft and within the air housing for diminishing leakage between the shaft and each respective housing.

* * * * *